United States Patent
Haudenschild et al.

(10) Patent No.: US 10,639,302 B2
(45) Date of Patent: *May 5, 2020

(54) USE OF CDK9 INHIBITORS TO REDUCE CARTILAGE DEGRADATION

(71) Applicant: THE REGENTS OF THE UNIVERSITY OF CALIFORNIA, Oakland, CA (US)

(72) Inventors: Dominik Haudenschild, Davis, CA (US); Paul Di Cesare, Sacramento, CA (US); Jasper Yik, Elk Grove, CA (US); Blaine Christiansen, Woodland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/196,955

(22) Filed: Nov. 20, 2018

(65) Prior Publication Data

US 2019/0255034 A1  Aug. 22, 2019

Related U.S. Application Data

(63) Continuation of application No. 15/356,231, filed on Nov. 18, 2016, now Pat. No. 10,172,844, which is a continuation of application No. 14/351,878, filed as application No. PCT/US2012/061079 on Oct. 19, 2012, now Pat. No. 9,498,471.

(60) Provisional application No. 61/549,741, filed on Oct. 20, 2011.

(51) Int. Cl.
| | | |
|---|---|---|
| A61K 31/453 | (2006.01) | |
| A61K 31/713 | (2006.01) | |
| A01N 1/02 | (2006.01) | |
| A61K 9/00 | (2006.01) | |

(52) U.S. Cl.
CPC .......... *A61K 31/453* (2013.01); *A01N 1/0226* (2013.01); *A61K 9/0019* (2013.01); *A61K 31/713* (2013.01)

(58) Field of Classification Search
CPC .. A61K 31/453; A61K 31/713; A61K 1/0226; A61K 9/0019
See application file for complete search history.

(56) References Cited

U.S. PATENT DOCUMENTS

| 6,436,915 B1 * | 8/2002 | Zhang ................. A61K 31/415 514/150 |
| 6,660,750 B2 | 12/2003 | Price et al. |
| 9,498,471 B2 | 11/2016 | Haudenschild et al. |
| 2005/0025765 A1 | 2/2005 | Dimauro et al. |
| 2006/0264628 A1 | 11/2006 | McInnes et al. |
| 2007/0021419 A1 | 1/2007 | Wang et al. |
| 2007/0021452 A1 | 1/2007 | Wang et al. |
| 2007/0072882 A1 | 3/2007 | Guzi et al. |
| 2007/0225270 A1 | 9/2007 | Guzi et al. |
| 2007/0275063 A1 | 11/2007 | Guzi et al. |
| 2008/0125404 A1 | 5/2008 | Benigni et al. |
| 2009/0012082 A1 | 1/2009 | Guicherit et al. |
| 2009/0137557 A1 | 5/2009 | Wang et al. |
| 2009/0162376 A1 | 6/2009 | Brown et al. |
| 2009/0215805 A1 | 8/2009 | Wood et al. |
| 2009/0258886 A1 | 10/2009 | Blanchard et al. |
| 2009/0270427 A1 | 10/2009 | Fisher et al. |
| 2009/0318441 A1 | 12/2009 | Brain et al. |
| 2009/0318446 A1 | 12/2009 | Fischer et al. |
| 2009/0325983 A1 | 12/2009 | Fischer et al. |
| 2010/0003246 A1 | 1/2010 | Hunag et al. |
| 2010/0035870 A1 | 2/2010 | Jones et al. |
| 2010/0076000 A1 | 3/2010 | Lucking et al. |
| 2010/0160350 A1 | 6/2010 | Kluge |
| 2010/0249149 A1 | 9/2010 | Allgeier et al. |
| 2012/0142680 A1 | 6/2012 | Blanchard et al. |
| 2012/0196855 A1 | 8/2012 | Blanchard et al. |
| 2012/0225899 A1 | 9/2012 | Costales et al. |
| 2015/0105423 A1 | 4/2015 | Haudenschild et al. |
| 2017/0304315 A1 | 10/2017 | Haudenschild et al. |

FOREIGN PATENT DOCUMENTS

| WO | WO 01/38377 | * | 5/2001 |
| WO | WO2001077080 | * | 10/2001 |
| WO | 2006021803 A2 | | 3/2006 |
| WO | 2006024858 A1 | | 3/2006 |
| WO | 2007117653 A2 | | 10/2007 |
| WO | 2008079933 A2 | | 7/2008 |
| WO | 2008129080 A1 | | 10/2008 |
| WO | WO 2009034411 | * | 3/2009 |
| WO | 2010020675 A1 | | 6/2010 |
| WO | 2011012661 A1 | | 2/2011 |
| WO | 2011077171 A1 | | 6/2011 |
| WO | 2012066065 A1 | | 5/2012 |
| WO | 2012066070 A1 | | 5/2012 |
| WO | 2012010164 A1 | | 8/2012 |
| WO | 2012010165 A2 | | 8/2012 |
| WO | 2012010166 A1 | | 8/2012 |
| WO | 2012101063 A1 | | 8/2012 |
| WO | 2013059634 A1 | | 4/2013 |
| WO | 2016061144 A1 | | 4/2016 |

OTHER PUBLICATIONS

International Search Report and Written Opinion dated Jan. 12, 2016 issued in International Application No. PCT/US15/55394.

(Continued)

*Primary Examiner* — Shirley V Gembeh
(74) *Attorney, Agent, or Firm* — Mintz, Levin, Cohn, Ferris, Glovsky and Popeo, P.C.

(57) ABSTRACT

The present invention relates to the use of cyclin-dependent kinase 9 (CDK9) inhibitors to reduce, inhibit and/or prevent cartilage degradation. CDK9 inhibitors can be used to reduce, inhibit and/or prevent cartilage degradation and loss of cartilage viability during allograft storage. CDK9 inhibitors can be used as a post-injury intervention treatment to reduce, inhibit and/or prevent the acute cellular responses that lead to future cartilage degradation and osteoarthritis.

23 Claims, 13 Drawing Sheets

(56) References Cited

OTHER PUBLICATIONS

International Preliminary Report on Patentability and Written Opinion dated Apr. 18, 2017 in International Application No. PCT/US15/55394.
International Search Report dated Mar. 28, 2013 issued in PCT/US2012/061079.
Written Opinion of the International Searching Authority dated Mar. 28, 2013 issued in PCT/US2012/061079.
International Preliminary Report on Patentability dated Apr. 12, 2014 issued in PCT/US2012/061079.
Anderson et al., "Post-Traumatic Osteoarthritis: Improved Understanding and Opportunities for Early Intervention," Journal of Orthopaedic Research, 2011, 29:802-809.
Byrd, et al., "Flavopiridol administered using a pharmacologically derived schedule is associated with marked clinical efficacy in refractory, genetically high-risk chronic lymphocytic leukemia," 2007, Blood Journal 109(2): 399-404.
Christiansen, B.A. et al., "Non-invasive mouse models of post-traumatic osteoarthritis," Osteoarthritis Cartilage, Oct. 2015; 23(10); Epub May 21, 2015.
Chu et al., "Osteoarthritis: From Palliation to Prevention," 2014, J Bone Joint Surg Am 96(e130):1-9.
Craft et al., "Physical Examination and Imaging of Medial Collateral Ligament and Posteromedial Corner of the Knee," 2015, Sports Med Arthrosc Rev 23(2):e1-e6.
De Falco, Giulia et al., "CDK9 (PITALRE): A Multifunctional cdc 2-Related Kinase," Journal of Cellular Physiology 177:501-506 (1998).
Fanelli et al., "Management of Chronic combined PCL Medial Posteromedial Instability of the Knee," 2015, Sports Med Arthrosc Rev 23(2):96-103.
Felson, D. T., "Osteoarthritis as a disease of mechanics," 2013, Osteoarthritis and Cartilage 21:20-12.
Haudenschild, Dominik R., "Reply to the Editor," Arthritis Rhemuamtol Letters, 2014, p. 3526.
Haudenschild, Dominik R., "Early Intervention with Cdk9 Inhibitors to Prevent Post-traumatic Osteoarthritis," Annual Report, OMB No. 0704-0188, Oct. 2013, pp. 1-136.
Heard et al., "Changes of early post-traumatic osteoarthritis in an ovine model of simulated ACL reconstruction are associated with transient acute post-injury synovial inflammation and tissue catabolism," 2013, Osteoarthritis and Cartilage 21:1942-1949.
Hu et al., "Inhibition of CDK9 prevents mechanical injury-induced inflammation, apoptosis and matrix degradation in cartilage explants," Eur Cell Matter, 2016; 30: 200-29, Feb. 11, 2016.
Krystof, Vladimir et al., "Perspective of Cyclin-dependent kinase 9 (CDK9) as a Drug Target," Current Pharmaceutical Design, 2012, 18, 2883-2890.

Nemeth at al., "Novel, selective CDK9 inhibitors for the treatment of HIV infection," 2011, Current Medical Chemistry, 18(3):342-358, Abstract Only, 2 pp.
Nowicki et al., "CDK9 Inhibitors Push Cancer Cells over the Edge," Oct. 29, 2010, Chemistry & Biology, 17:1047-1048.
Pelletier et al., "Osteoarthritis, an Inflammatory Disease: Potential Implication for the Selection of New Therapeutic Targets," 2001, Arthritis & Rheumatism 44(6):1237-1247.
Phelps et al. "Clinical response and pharmacokinetics from a phase 1 study of an active dosing schedule of flavopiridol in relapsed chronic lymphocytic leukemia," 2009, Blood Journal, 113:2637-2645.
Ramaswamy et al., "A dose-finding, pharmacokinetic and pharmacodynamics study of a novel schedule of flavopiridol in patients with advance solid tumors," 2012, Invest New Drugs 30(2):629-638, Abstract Only.
Schmerwitz et al., "Flavopiridol Protects Against Inflammation by Attenuating Leukocyte-Endothelial Interaction via Inhibition of Cyclin-Dependent Kinase 9," 2011, Arterioscler Thromb Vasc Biol, pp. 280-288.
Schmerwitz Ulrike Karla Ilse, "Novel mechanisms of flavopiridol: protection against inflammation-induced endothelium-leukocyte interactions in vivo and in vitro," 2010, Dissertation zur Erlangung des Doktorgrades der Fakultat fur Chemie und Pharmazie der Ludwig-Maximilians-Universitat Munchen, pp. 1-113.
Sczcodry et al., "Progressive Chondrocyte Death After Impact Injury Indicates a Need for Chondroprotective Therapy," 2009, Am J Sports Med. 37(12):2318-2322.
Sekeine et al., The J. of Immunology, 2008: 1954-1961.
Tam et al., Journal of Orthopedic Research 2007, 1136-1144.
Tsuchida et al., "Cytokine profiles in the joint depend on pathology, but are different between synovial fluid, cartilage issue and cultured chondrocytes," 2014, Arthritis Research & Therapy, 16(441):1-15.
Wassilew et al., "The expression of proinflammatory cytokines and matrix metalloproteinases in the synovial membranes of patients with osteoarthritis compared with traumatic knee disorders," 2010, Arthroscopy 26 (8):1096-1104.
Wen et al., "Does post injury ACL reconstruction prevent future OA?," 2014, Nature Reviews/Rheumatology, 10:577-578.
Yik et al. "Discoveries in Molecular and Biomechanical Research," 2011, Research Symposium, pp. 1-28.
Yik et al. "The cdk9 inhibitor flavopiridol effectively suppresses the activation of primary inflammatory response genes in human articular chondrocytes," 2012, Orthopaedic Research Society (ORS) 2012 meeting, Feb. 4-7, 2012.
Yik et al., "Cyclin-Dependent Kinase 9 Inhibition Protects Cartilage From the Catabolic Effects of Proinflammatory Cytokines," 2014, Arthritis & Rheumatology, 66(6):1537-1546.

* cited by examiner

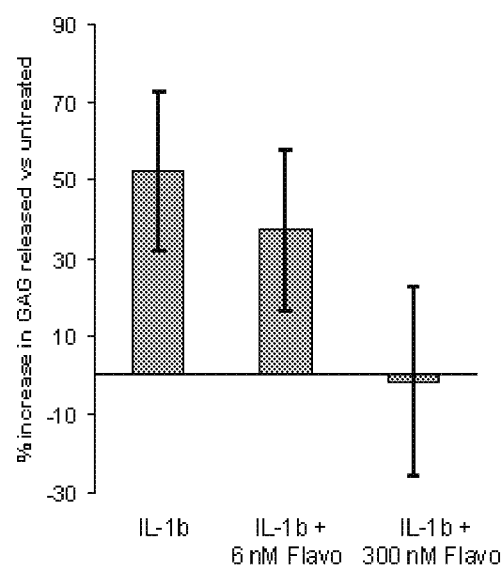 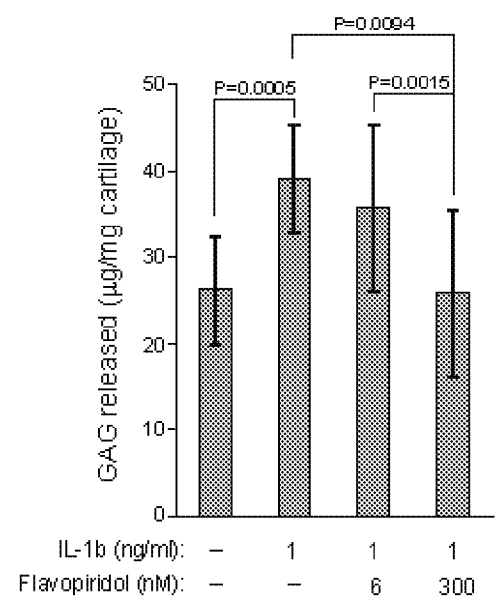
*Fig. 7A-B*

USE OF CDK9 INHIBITORS TO REDUCE CARTILAGE DEGRADATION

CROSS-REFERENCE TO RELATED APPLICATIONS

This application is a continuation of U.S. application Ser. No. 15/356,231, filed Nov. 18, 2016, which is a continuation of U.S. application Ser. No. 14/351,878, filed on Apr. 15, 2014, now U.S. Pat. No. 9,498,471, which is a U.S. national phase under 35 U.S.C. § 371 of Intl. Appl. No. PCT/US2012/061079, filed on Oct. 19, 2012, which claims the benefit of under 35 U.S.C. § 119(e) of U.S. Provisional Application No. 61/549,741, filed on Oct. 20, 2011, which are hereby incorporated herein by reference in their entireties for all purposes.

STATEMENT OF GOVERNMENTAL SUPPORT

This work was supported inpart by Grrant No. 1R21AR063348 from the National Institutes of Health. The Government has certain rights in this invention.

FIELD

The present invention relates to the use of cyclin-dependent kinase 9 (CDK9) inhibitors to reduce, inhibit and/or prevent cartilage degradation. CDK9 inhibitors can be used to reduce, inhibit and/or prevent cartilage degradation and loss of cartilage viability during allograft storage. CDK9 inhibitors can be used as a post-injury intervention treatment to reduce, inhibit and/or prevent the acute cellular responses that lead to future cartilage degradation and osteoarthritis.

BACKGROUND

A host of pro-inflammatory and cellular stress induces inflammatory response in chondrocytes, leading to upregulation of matrix metalloproteinases (MMPs) and aggrecanases that degrade the cartilage matrix. Chronic deregulation of these catabolic pathways is suspected of causing osteoarthritis. Regardless of the sources of inflammation, the downstream signals all converge on a common mechanism that activates transcription of all primary response genes. This regulatory point is controlled by the transcription factor cyclin-dependent kinase 9 (CDK9) and its T-type cyclin partner. It was believed for many years that the rate-limiting step in transcriptional activation is the recruitment of transcription factors and RNA Polymerase II (Pol II) to gene promoters. However, recent studies on primary response genes have shown that in their basal and unstimulated states, Pol II is already pre-assembled but is paused at the promoters (Hargreaves, et al., *Cell* 2009, 138:129-45; Zippo, et al., *Cell* 2009, 138:1122-36). The rapid activation of these genes is the result of signal-induced recruitment of CDK9 to the promoters, where it phosphorylates Pol II. Phosphorylation by CDK9 induces a conformational change that allows Pol II to enter possessive elongation to efficiently transcribe full-length mRNAs (Zhou and Yik, *MMBR* 2006, 70(3): 646-659). Given that CDK9 controls a common mechanism of transcriptional activation of inducible genes, it is an effective target for inhibiting the undesirable inflammatory responses from diverse cellular stress, such as sports-related injuries. The present invention is based, in part, on the discovery that pharmacological CDK9 inhibitors, e.g., flavopiridol, and analogs and salts thereof, can effectively suppress primary inflammatory genes in human articular chondrocytes in vitro. Effective suppression of inflammatory responses allows for longer storage life for osteochondral explants used commonly in cartilage repair, and also has therapeutic implications in preventing cartilage breakdown in post-traumatic osteoarthritis.

SUMMARY

In one aspect, the invention provides methods of reducing, preventing or inhibiting cartilage degradation and/or chondrocyte death in a subject in need thereof. In some embodiments, the methods comprise administering to the subject an effective amount of an inhibitor of cyclin-dependent kinase 9 (CDK9), thereby reducing, preventing or inhibiting cartilage degradation and/or chondrocyte death in the subject.

In a further aspect, the invention provides methods of reducing, preventing, delaying or inhibiting the onset and/or progression of post-traumatic osteoarthritis in a subject in need thereof. In some embodiments, the methods comprise administering to the subject an effective amount of an inhibitor of cyclin-dependent kinase 9 (CDK9), thereby reducing, preventing or inhibiting post-traumatic osteoarthritis in the subject.

In some embodiments, the subject has experienced a traumatic injury to cartilage tissue. In some embodiments, the subject has undergone or received joint surgery (which can inflict traumatic injury to cartilage). In some embodiments, the inhibitor of CDK9 is administered within 10 days, e.g., within 9, 8, 7, 6, 5, 4, 3, 2, 1 days, e.g., within 24, 20, 18, 16, 14, 12, 10, 9, 8, 7, 6, 5, 4, 3, 2, 1 hours after experiencing traumatic injury. In some embodiments, the subject has undergone surgery to repair damaged cartilage tissue. In some embodiments, the subject has received an osteochondral explant, e.g., a cartilage allograft. In some embodiments, the inhibitor of CDK9 is administered concurrently with or prior to surgery. In some embodiments, the inhibitor of CDK9 is administered within 10 days, e.g., within 9, 8, 7, 6, 5, 4, 3, 2, 1 days, e.g., within 24, 20, 18, 16, 14, 12, 10, 9, 8, 7, 6, 5, 4, 3, 2, 1 hours after surgery. In some embodiments, the inhibitor of CDK9 is administered over a course of 10 days, e.g., over 9, 8, 7, 6, 5, 4, 3, 2, 1 days. In various embodiments, the inhibitor of CDK9 is administered every 2 days, every day, or twice daily, as appropriate.

In some embodiments, the inhibitor of CDK9 is administered systemically. In some embodiments, the inhibitor of CDK9 is administered directly to the lesion, e.g., to the site of injured cartilage tissue.

In some embodiments, the inhibitor of CDK9 is a small organic compound, e.g., flavopiridol, and analogs and salts thereof. In some embodiments, the inhibitor of CDK9 is an inhibitory nucleic acid. In varying embodiments, the inhibitor of CDK9 is flavopiridol and is administered intravenously.

In another aspect, the invention provides methods of reducing, preventing or inhibiting degradation of an osteochondral explant (e.g., ex vivo cartilage tissue) and/or chondrocyte death during storage. In some embodiments, the methods comprise storing the cartilage in a solution comprising an effective amount of an inhibitor of cyclin-dependent kinase 9 (CDK9). In some embodiments, the osteochondral explant is allograft cartilage. In some embodiments, the inhibitor of CDK9 is a small organic compound, e.g., flavopiridol, and analogs and salts thereof. In some embodiments, the osteochondral explant is submerged in the solution comprising the inhibitor of CDK9. In some embodiments, the solution comprises flavopiridol, or an analog or salt thereof, at a concentration in the range of about 100 nM to about 1000 nM, e.g., about 300 nM. The solution may contain additional pharmaceutically acceptable excipients, described herein.

In a related aspect, the invention provides compositions comprising an osteochondral explant (e.g., ex vivo cartilage tissue) in a solution comprising an inhibitor of cyclin-dependent kinase 9 (CDK9). In some embodiments, the osteochondral explant is allograft cartilage. In some embodiments, the inhibitor of CDK9 is a small organic compound, e.g., flavopiridol, and analogs and salts thereof. In some embodiments, the osteochondral explant is submerged in the solution comprising the inhibitor of CDK9. In some embodiments, the solution comprises flavopiridol, or an analog or salt thereof, at a concentration in the range of about 100 nM to about 1000 nM, e.g., about 300 nM. In varying embodiments, the solution is a physiologically isotonic solution. In varying embodiments, the solution is an aqueous solution. The solution may contain additional pharmaceutically acceptable excipients, described herein. In some embodiments, the composition is provided as a packaged kit.

Definitions

The term "cyclin-dependent kinase 9" or "CDK9" refers to a member of the cyclin-dependent protein kinase (CDK) family. CDK family members are highly similar to the gene products of S. cerevisiae cdc28, and S. pombe cdc2, and known as important cell cycle regulators. CDK9 was found to be a component of the multiprotein complex TAK/P-TEFb, which is an elongation factor for RNA polymerase II-directed transcription and functions by phosphorylating the C-terminal domain of the largest subunit of RNA polymerase II. CDK9 forms a complex with and is regulated by its regulatory subunit cyclin T or cyclin K. HIV-1 Tat protein was found to interact with this protein and cyclin T. Structurally, "CDK9" refers to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 400, or more amino acids, or over the full-length, to an amino acid sequence encoded by a CDK9 nucleic acid (see, e.g., GenBank Accession No. NM_001261.3); (2) bind to antibodies, e.g., polyclonal antibodies, raised against an immunogen comprising an amino acid sequence of a CDK9 polypeptide (e.g., GenBank Accession No. NP_001252.1); or an amino acid sequence encoded by a CDK9 nucleic acid (e.g., CDK9 polynucleotides described herein), and conservatively modified variants thereof; (3) specifically hybridize under stringent hybridization conditions to an anti-sense strand corresponding to a nucleic acid sequence encoding a CDK9 protein, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a CDK9 nucleic acid (e.g., CDK9 polynucleotides, as described herein, and CDK9 polynucleotides that encode CDK9 polypeptides, as described herein). Based on the knowledge of CDK9 homologs, those of skill can readily determine residue positions that are more tolerant to substitution. For example, amino acid residues conserved amongst species are less tolerant of substitution or deletion. Similarly, amino acid residues that are not conserved amongst species are more tolerant of substitution or deletion, while retaining the function of the CDK9 protein.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);
6) Phenylalanine (F), Tyrosine (Y), Tryptophan (W); and
7) Serine (S), Threonine (T)

(see, e.g., Creighton, Proteins (1984)).

The terms "identical" or percent "identity," and variants thereof in the context of two or more polypeptide sequences, refer to two or more sequences or subsequences that are the same. Sequences are "substantially identical" if they have a specified percentage of amino acid residues or nucleotides that are the same (i.e., at least 60% identity, optionally at least 65%, 70%, 75%, 80%, 85%, 90%, 95%, 96%, 97%, 98%, or 99% identity over a specified region (or the whole reference sequence when not specified)), when compared and aligned for maximum correspondence over a comparison window, or designated region as measured using one of the following sequence comparison algorithms or by manual alignment and visual inspection. The present invention provides polypeptides substantially identical to CDK9, as described herein. Optionally, the identity exists over a region that is at least about 50 amino acids in length, or more preferably over a region that is 100 to 500 or 1000 or more amino acids in length, or over the full-length of the sequence.

The terms "similarity," or "percent similarity," and variants thereof in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, 95%, 96%, 97%, 98% or 99% similar over a specified region), when compared and aligned for maximum correspondence over a comparison window, or designated region as measured using one of the following sequence comparison algorithms or by manual alignment and visual inspection. Sequences having less than 100% similarity but that have at least one of the specified percentages are said to be "substantially similar." Optionally, this identity exists over a region that is at least about 50 amino acids in length, or more preferably over a region that is at least about 100 to 500 or 1000 or more amino acids in length, or over the full-length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window", and variants thereof, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can also be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), Karlin and Altschul Proc. Natl. Acad. Sci. (U.S.A.) 87:2264-2268 (1990), or by manual alignment and visual inspection (see, e.g., Ausubel et al., Current Protocols in Molecular Biology (1995 supplement)).

Examples of an algorithm that is suitable for determining percent sequence identity and sequence similarity include the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (on the internet at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Standard BLAST algorithm parameters have an expected threshold of 10 (according to the stochastic model of Karlin and Altschul (PNAS, 87:2264-2268 (1990)); a word size of 28; reward and penalty of 1/−2 (a ratio of 0.5, or 1/−2, is used for sequences that are 95% conserved); and a linear GAP cost.

The term "effective amount" refers to an amount (here of an inhibitor of CDK9) which provides either subjective relief of a symptom(s) or an objectively identifiable improvement as noted by the clinician or other qualified observer. Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics*, 11th Edition, 2006, supra; in a Physicians' Desk Reference (PDR), 64$^{th}$ Edition, 2010; in *Remington: The Science and Practice of Pharmacy*, 21$^{st}$ Ed., 2006, supra; and in *Martindale: The Complete Drug Reference*, Sweetman, 2005, London: Pharmaceutical Press., and in Martindale, *Martindale: The Extra Pharmacopoeia*, 31st Edition., 1996, Amer Pharmaceutical Assn, each of which are hereby incorporated herein by reference.

The terms "treating" and "treatment" and variants thereof refer to promoting healing, delaying the onset of, retarding or reversing the progress of, alleviating or preventing either the disease or condition to which the term applies (e.g., cartilage degradation), or one or more symptoms of such disease or condition. Treating and treatment encompass both therapeutic and prophylactic treatment regimens.

The terms "subject," "patient," or "individual" interchangeably refer to any mammal, for example, humans and non-human primates, domestic mammals (e.g., canine, feline), agricultural mammals (e.g., bovine, equine, ovine, porcine) and laboratory mammals (e.g., mouse, rat, rabbit, hamster).

As used herein, "administering" refers to local and systemic administration, e.g., including enteral, parenteral, pulmonary, and topical/transdermal administration. Routes of administration for compounds (e.g., inhibitors of CDK9, e.g., flavopiridol, and analogs and salts thereof) that find use in the methods described herein include, e.g., oral (per os (P.O.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The term "co-administering" or "concurrent administration", when used, for example with respect to the compounds (e.g., inhibitors of CDK9, e.g., flavopiridol, and analogs and salts thereof) and/or analogs thereof and another active agent, refers to administration of the compound and/or analogs and the active agent such that both can simultaneously achieve a physiological effect. The two agents, however, need not be administered together. In certain embodiments, administration of one agent can precede administration of the other. Simultaneous physiological effect need not necessarily require presence of both agents in the circulation at the same time. However, in certain embodiments, co-administering typically results in both agents being simultaneously present in the body (e.g., in the plasma) at a significant fraction (e.g., 20% or greater, preferably 30% or 40% or greater, more preferably 50% or 60% or greater, most preferably 70% or 80% or 90% or greater) of their maximum serum concentration for any given dose. For example, in various embodiments, an inhibitor of CDK9 is co-administered with protein complexes or protein scaffolds comprising one or more monomers of cartilage oligomeric matrix protein (COMP) bound to one or more growth factors, as described in co-owned and co-pending International Appl. No. PCT/US2011/051610.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

BRIEF DESCRIPTION OF THE DRAWINGS

FIGS. 7A and 7B illustrate that CDK9 inhibition prevents IL-1β induced GAG breakdown in cartilage. Human cartilage explants (n=5) were treated with 1 ng/ml IL-1β and the indicated concentrations of Flavopiridol for 6 days (media change at day 3). FIG. 7A shows the results of GAG released into the medium was measured by DMMB assays and normalized to the wet weight of the explants. FIG. 7B shows the results that treatment with IL-1β alone caused cartilage degradation as indicated by increased GAG release. In the presence of Flavopiridol, GAG release returned to baseline.

DETAILED DESCRIPTION

1. Introduction

Figure 1:
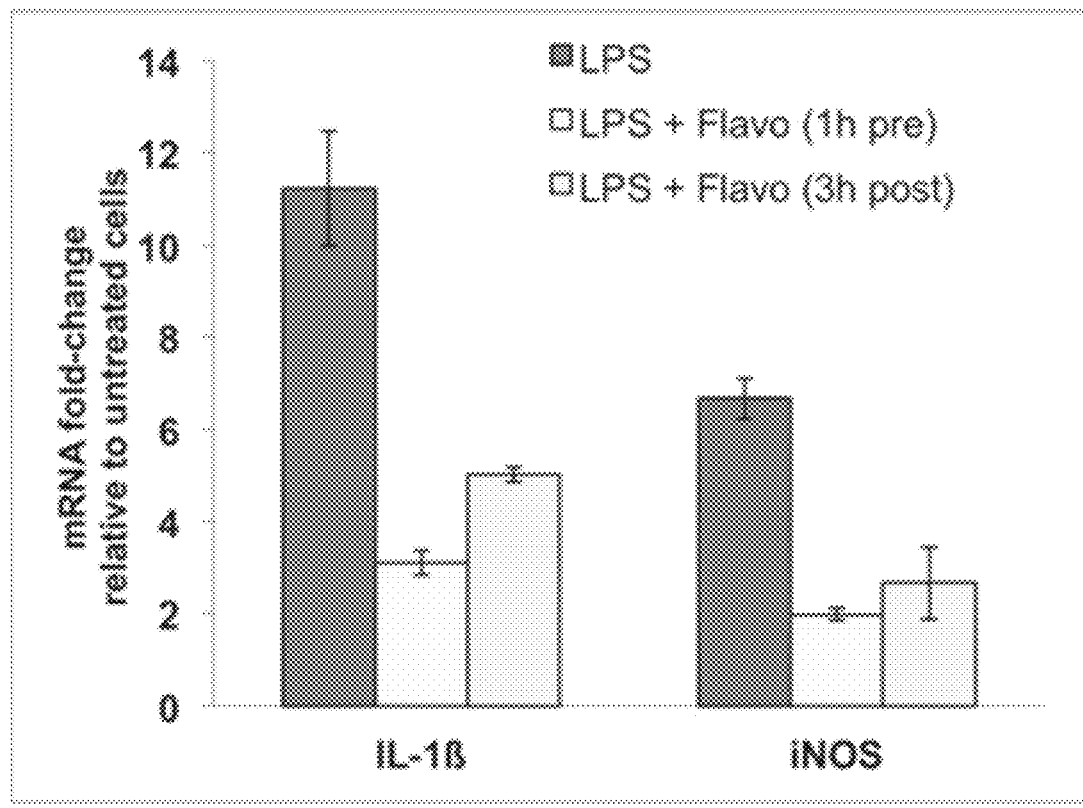
FIG. 1 illustrates that flavopiridol suppresses LPS-induced inflammatory response. First-passage human chondrocytes grown in monolayer culture were given a strong inflammatory insult consisting of 10 ng/ml lipopolysaccharides (LPS) for 5 hours. This induced transcriptional activation of the primary response genes IL-1β and iNOS. Pre-treatment with 300 nM flavopiridol strongly attenuated transcriptional activation of both primary response genes by LPS. The effect of CDK9 inhibition on transcription of 3 hours after the addition of LPS was also tested. Inhibition of CDK9 three hours after the inflammatory insult similarly attenuated the transcriptional activation of primary response genes IL-1β and iNOS, showing that the window for therapeutic intervention can be at least 3 hours after a joint injury event, making it a practical therapeutic strategy.

The present invention is based, in part, on the discovery that intervening with CDK9 activity finds us to preserve cartilage after injury (e.g., traumatic injury and/or surgical injury) and during storage (e.g., allograft storage). Any inhibitor of CDK9 known in the art can be used in the present methods, including inhibitory nucleic acids and inhibitory compounds (e.g., flavopiridol, and analogs and salts thereof).

Many different stimuli can induce inflammation, and several of these are being investigated individually as arthritis drugs (e.g., IL-1 antagonists, TNF antagonists, anti-oxidants). The focus has been on inhibition of the pathway so that transcription of response genes does not occur. None of these existing investigations have addressed the process of transcription. The present invention is based, in part, on the discovery that all of these pathways converge on the activation of CDK9 for the transcriptional elongation of the primary response genes. Inhibition of the transcriptional elongation by CDK9 is limited to the primary response inflammatory genes, and CDK9 inhibition does not affect transcription of housekeeping genes, and therefore is not detrimental to cells or tissues in the short term. The advantage of CDK9 inhibition is that it reduces transcriptional elongation of inflammatory genes from all inflammatory stimuli. In various embodiments, CDK9 can be specifically and reversibly inhibited, e.g., with small-molecule drugs (e.g., flavopiridol and other known CDK9 inhibitors, and analogs and salts thereof) and inhibitory nucleic acids (e.g., siRNA, miRNA, antisense RNA).

Symptomatic osteoarthritis (OA) can be defined as the end-stage failure of load bearing joints at the organ level (1). While the etiology of OA remains incompletely understood, it is well established that joint injuries often progress to OA over time (2). High-energy joint traumas that cause intra-articular fractures often result in the rapid development of joint degradation and post-traumatic osteoarthritis (PTOA) (3). Even lower-energy traumas to the joint, which are much more common, will initiate slowly progressing cartilage and joint degradation that results in symptomatic PTOA many years later (2). As an example, from a total of 900,000 knee injuries annually in the United States(4), the American Academy of Orthopaedic Surgeons estimates 200,000 injuries of the anterior cruciate ligament (ACL) in the general population (5), including 2500 to 3000 ACL reconstructions in military patients (6). Strikingly, approximately 50% of these ACL injury patients will develop knee PTOA after a 10- to 20-year asymptomatic lag phase (7). NFL retirees under the age of 50 are five times more likely to have arthritis than comparable men in the general population, approximately 80% of retirees report having joint pain lasting most of the day, and over 23% of NFL retirees over 50 years of age have had a joint replacement.

Despite a lack of joint pain during the asymptomatic lag phase, progressive deterioration of bone and cartilage begins to develop soon after traumatic joint injury. In OA of the knee or hip joints, the asymptomatic cartilage degeneration phase can last many years or even decades (8). By the time arthritic joints become painful, there is often widespread cartilage damage with areas of complete cartilage loss. As a result of the extended painless "pre-OA" condition, the typical OA patient is seen in the clinic only after extensive joint damage has already occurred. At these late stages, treatment of the underlying causes of joint degeneration is no longer possible and the damage has become irreversible. Current OA treatments address the associated joint pain, but do not improve joint function or alter the underlying pathology. When these palliative treatments eventually fail, invasive surgical joint replacement is the only remaining treatment for pain-free ambulation. Although there is abundant evidence that joint traumas such as anterior cruciate ligament (ACL) tears will ultimately lead to OA (9-11), current clinical treatment does nothing at the time of these injuries to prevent the future onset of OA. Currently, clinical treatment is aimed at reducing the immediate pain and swelling in the joint and restoring normal joint movement. The most common recommendations are to apply ice, gently compress the joint with an elastic bandage, and take pain medications such as aspirin, acetaminophen, or ibuprofen. Importantly, these treatments do not address the initiation of OA. The incidence of OA is independent of whether patients undergo surgical reconstruction of the ACL (7,12), suggesting that the injury event, in addition to the chronic joint instability, has a causative role in OA pathogenesis.

The mechanical damage that a joint experiences during an impact has immediate effects on the tissues: cell death and physical damage to the joint tissues occur within milliseconds of impact. The immediate mechanical damage then triggers an acute cellular response, which occurs within a time-scale of minutes to hours (13). The acute response phase is characterized by the release of inflammatory mediators from the injured joint tissues, including IL-1, IL-6, iNOS, and TNF-α (13,14). This causes the transcriptional activation of primary response genes (or inflammatory genes), and leads to increased production of matrix degrading enzymes such as MMPs, collagenases, aggrecanases, and cathepsins. The enzymatic degradation of matrix contributes to OA via a cascade of destructive events, including:
(1) reducing the stiffness and elasticity of cartilage, thus increasing the mechanical stresses on chondrocytes,
(2) increasing the hydraulic permeability of cartilage, leading to loss of interstitial fluid and increased diffusion of solutes (i.e. degradative enzymes, proteoglycans),
(3) increasing the accessibility of remaining cartilage matrix structures to enzymatic digestion,
(4) thickening of the subchondral bone plate,
(5) structural changes to the trabecular bone, and
(6) formation of osteophytes and heterotopic bone (8).

We believe that a window for therapeutic intervention exists shortly after injury, during which attenuating the acute cellular response decreases production of matrix degrading enzymes and thus decreases the likelihood of developing post-traumatic osteoarthritis (PTOA).

The transcriptional activation of primary response genes is an important step of the acute cellular response to injury. Transcriptional activation of primary response genes occurs in a timeframe of minutes to hours after the injury event. The majority of the primary response genes are 'primed' for transcription at a moment's notice, with the transcription complex already assembled on the promoters and the RNA polymerase complex stalled just before entering the transcription elongation stage. In a recent Cell paper, Hargreaves et al elegantly demonstrated that the rate-limiting step in transcriptional elongation of primary response genes is the recruitment of cyclin-dependent kinase-9 (CDK9) (15). In the case of inflammatory gene transcription, CDK9 is recruited to the transcription complex by NFκB (16,17). Importantly, CDK9 kinase activity is required for transcription of the primary response inflammatory genes to proceed, and this mechanism of regulation is conserved amongst primary response genes (18). Thus, CDK9 kinase activity represents a new molecular target to inhibit the acute inflammatory response after joint injury.

2. Subjects Who May Benefit

Subjects who can benefit from a regime of CDK9 inhibitors generally have experienced or imminently will experience an injury to cartilage tissue. For example, the subject may have experienced an injury (e.g., a traumatic injury) that damages cartilage tissue. The subject may also undergo or have undergone surgery to repair damaged cartilage tissue and/or to receive an osteochondral explant.

In various embodiments, a regime of a CDK9 inhibitor is administered to the subject within about 10 days after damage or injury to cartilage tissue, for example, within about 9, 8, 7, 6, 5, 4, 3, 2 or 1 days after damage or injury to cartilage tissue. In various embodiments, a regime of a CDK9 inhibitor is administered to the subject within about 24 hours after damage or injury to cartilage tissue, for example, within about 22, 20, 18, 16, 14, 12, 10, 9, 8, 7, 6, 5, 4, 3, 2 or 1 hours after damage or injury to cartilage tissue.

3. Inhibitors of CDK9

Generally, the activity of a CDK9, e.g., a polypeptide having at least 80% sequence identity, e.g., at least about 85%, 90%, 91%, 92%, 93%, 94%, 95%, 96%, 97%, 98% or 99% sequence identity, to an amino acid sequence of NP_001252.1, is inhibited or reduced, thereby preventing, reducing, delaying or inhibiting degradation of cartilage and/or onset or progression of post-traumatic osteoarthritis.

a. Small Organic Compounds

CDK9 is a member of the cyclin-dependent kinase family, and most proteins in this family regulate cell-cycle progression. Over the last 2 decades there has been intense research into CDK inhibitors as anti-proliferative agents that arrest cell cycle progression in cancers, and numerous CDK inhibitors are in phase II and III clinical trials (19,20). CDK9, unlike most CDK proteins that regulate cell cycle progression, is mainly thought to regulate RNA synthesis and transcriptional elongation (21). There are small-molecule inhibitors with relatively good specificity for CDK9, including flavopiridol, and analogs and salts thereof. Commercial preparations of flavopiridol are called Alvocidib The IUPAC name for flavopiridol is 2-(2-chlorophenyl)-5,7-dihydroxy-8-[(3S,4R)-3-hydroxy-1-methyl-4-piperidinyl]-4-chromenone). The structure of flavopiridol is shown below.

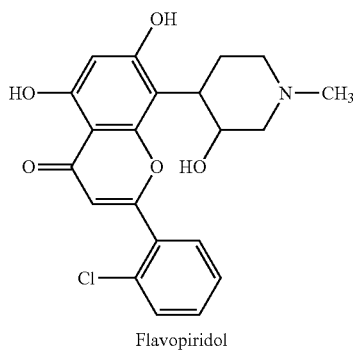 [SMILES: CN1CCC(c2c(O)cc(O)c3c(=O)cc(-c4ccccc4Cl)oc23)C(O)C1]

Flavopiridol

Flavopiridol inhibits CDK9 kinase activity by a high affinity (Kd=3 nM to 6 nM) interaction with the ATP-binding pocket of CDK9 (22,23). Inhibition of CDK9 kinase activity prevents transcriptional activation of primary response genes by preventing transcriptional elongation (15). Systemic administration of flavopiridol is well tolerated, and clinical trials with flavopiridol are successful in treating refractory chronic lymphocytic leukemia (24-26). Recently, Sekine et al have taken advantage of the anti-proliferative effects of flavopiridol in mouse models of rheumatoid arthritis (RA). They demonstrated that flavopiridol reduced synovial hyperplasia and effectively prevented rheumatoid arthritis (27). The anti-arthritic effect was reversible; when flavopiridol treatment was stopped, synovial hyperplasia resumed and RA progressed rapidly.

Other CDK inhibitors that can find use include without limitation, e.g., 4-(3,5-Diamino-1H-pyrazol-4-ylazo)-phenol (Calbiochem Catalog No. 238811), 2-(Pyridin-4-yl)-1,5,6,7-tetrahydro-4H-pyrrolo[3,2-c]pyridinone, PHA-767491 (Calbiochem Catalog No. 217707), and those described, e.g., in International Publication Nos. WO 2012/101066 (pyridine biaryl amine compounds); WO 2012/101065 (pyrimidine biaryl amine compounds); WO 2012/101064 (N-acyl pyrimidine biaryl compounds); WO 2012/101063 (N-acyl pyridine biaryl compounds); WO 2012/066070 (3-(aminoaryl)-pyridine compounds); WO 2012/066065 (phenyl-heteroaryl amine compounds); WO 2011/012661 (pyridine and pyrazine derivatives); WO 2011/077171 (4-phenylamino-pyrimidine derivatives); WO 2010/020675 (pyrrolopyrimidine compounds); WO 2008/079933 (heteroaryl-heteroaryl compounds); WO 2007/117653 (CDK9-PI3K-AKT inhibitors); WO 2006/024858 (4-arylazo-3,5-diamino-pyrazole compounds); WO 2006/021803 (purine and pyrimidine CDK inhibitors) and in U.S. Patent Publication Nos. 2012/0225899; 2012/0196855; 2012/0142680; 2010/0160350; 2010/0249149; 2010/0076000; 2010/0035870; 2010/0003246; 2009/0325983; 2009/ 0318446; 2009/0318441; 2009/0270427; 2009/0258886; 2009/0215805; 2009/0215805; 2009/0137572; 2008/0125404; 2007/0275963; 2007/0225270; 2007/0072882; 2007/0021452; 2007/0021419; and 2006/0264628, all of which are hereby incorporated herein by reference in their entirety for all purposes.

b. Inhibitory Nucleic Acids

Decreasing or inhibiting CDK9 gene expression can be achieved using any method in the art, including through the use of inhibitory nucleic acids (e.g., small interfering RNA (siRNA), micro RNA (miRNA), antisense RNA, ribozymes, etc.). Inhibitory nucleic acids can be single-stranded nucleic acids that can specifically bind to a complementary nucleic acid sequence. By binding to the appropriate target sequence, an RNA-RNA, a DNA-DNA, or an RNA-DNA duplex or triplex is formed. Such inhibitory nucleic acids can be in either the "sense" or "antisense" orientation. See, for example, Tafech, et al., Curr Med Chem (2006) 13:863-81; Mahato, et al., Expert Opin Drug Deliv (2005) 2:3-28; Scanlon, Curr Pharm Biotechnol (2004) 5:415-20; and Scherer and Rossi, Nat Biotechnol (2003) 21:1457-65.

In one embodiment, the inhibitory nucleic acid can specifically bind to a target nucleic acid sequence or subsequence that encodes a CDK9. Administration of such inhibitory nucleic acids can decrease or inhibit the activity of CDK9 and consequently, cartilage degradation. Nucleotide sequences encoding CDK9 are known for several mammalian species, including human, e.g., NM_001261.3. From known CDK9 nucleotide sequences, one can derive a suitable inhibitory nucleic acid.

1. Antisense Oligonucleotides

In some embodiments, the inhibitory nucleic acid is an antisense molecule. Antisense oligonucleotides are relatively short nucleic acids that are complementary (or antisense) to the coding strand (sense strand) of the mRNA encoding a CDK9. Although antisense oligonucleotides are typically RNA based, they can also be DNA based. Additionally, antisense oligonucleotides are often modified to increase their stability.

Without being bound by theory, the binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding CDK9. Accordingly, antisense oligonucleotides decrease the expression and/or activity of CDK9.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO 88/09810) or the blood-brain barrier (see, e.g., PCT Publication No. WO 89/10134), hybridization-triggered cleavage agents (See, e.g., Krol et al., 1988, BioTechniques 6:958-976) or intercalating agents. (See, e.g., Zon, 1988, Pharm. Res. 5:539-549). To this end, the oligonucleotide can be conjugated to another molecule.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an anomeric oligonucleotide. An anomeric oligonucleotide forms specific double-stranded hybrids with complementary RNA in which, contrary to the usual-units, the strands run parallel to each other (Gautier et al., 1987, Nucl. Acids Res. 15:6625-6641). The oligonucleotide is a 2'-O-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

The selection of an appropriate oligonucleotide can be readily performed by one of skill in the art. Given the nucleic acid sequence encoding a CDK9, one of skill in the art can design antisense oligonucleotides that bind to a target nucleic acid sequence and test these oligonucleotides in an in vitro or in vivo system to confirm that they bind to and mediate the degradation of the mRNA encoding the CDK9. To design an antisense oligonucleotide that specifically binds to and mediates the degradation of a CDK9 encoding nucleic acid, it is preferred that the sequence recognized by the oligonucleotide is unique or substantially unique to the CDK9 to be inhibited. For example, sequences that are frequently repeated across an encoding sequence may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a CDK9.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

2. Small Interfering RNA (siRNA or RNAi)

In some embodiments, the inhibitory nucleic acid is a small interfering RNA (siRNA or RNAi) molecule. RNAi constructs comprise double stranded RNA that can specifically block expression of a target gene. "RNA interference" or "RNAi" is a term initially applied to a phenomenon where double-stranded RNA (dsRNA) blocks gene expression in a specific and post-transcriptional manner. RNAi provides a useful method of inhibiting gene expression in vitro or in vivo. RNAi constructs can include small interfering RNAs (siRNAs), hairpin RNAs, and other RNA species which can be cleaved in vivo to form siRNAs. RNAi constructs herein also include expression vectors ("RNAi expression vectors") capable of giving rise to transcripts which form dsRNAs or hairpin RNAs in cells, and/or transcripts which can produce siRNAs in vivo.

RNAi expression vectors express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell.

The RNAi constructs contain a nucleotide sequence that hybridizes under physiologic conditions of the cell to the nucleotide sequence of at least a portion of the mRNA transcript for the gene to be inhibited (i.e., a CDK9-encoding nucleic acid sequence). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity can be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, for example, 95%, 96%, 97%, 98%, 99%, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO 01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO 01/68836 and WO 01/75164.

Exemplary RNAi constructs that specifically recognize a particular gene, or a particular family of genes can be selected using methodology outlined in detail above with respect to the selection of antisense oligonucleotide. Similarly, methods of delivery RNAi constructs include the methods for delivery antisense oligonucleotides outlined in detail above.

3. Ribozymes

In some embodiments, the inhibitory nucleic acid is a ribozyme. Ribozymes molecules designed to catalytically cleave an mRNA transcripts can also be used to prevent translation of mRNA (See, e.g., PCT International Publication WO 90/11364; Sarver et al., 1990, Science 247:1222-1225 and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; WO 88/04300; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and can be delivered to cells in vitro or in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid.

There are currently two basic types of DNA enzymes, and both of these were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence.

When synthesizing the DNA enzyme, the specific antisense recognition sequence that will target the enzyme to the message is divided so that it comprises the two arms of the DNA enzyme, and the DNA enzyme loop is placed between the two specific arms.

Methods of making and administering DNA enzymes can be found, for example, in U.S. Pat. No. 6,110,462. Similarly, methods of delivery DNA ribozymes in vitro or in vivo include methods of delivery RNA ribozyme, as outlined in detail above. Additionally, one of skill in the art will recognize that, like antisense oligonucleotide, DNA enzymes can be optionally modified to improve stability and improve resistance to degradation.

4. Formulation and Administration

In therapeutic applications, the CDK9 inhibitors can be administered to an individual who has suffered a traumatic injury to cartilage tissue, who has undergone surgery to repair cartilage tissue and/or who has received a cartilage allograft. Compositions that contain CDK9 inhibitors are administered to a patient in an amount sufficient to suppress the undesirable inflammation and to eliminate or at least partially arrest symptoms and/or complications. An amount adequate to accomplish this is defined as a "therapeutically effective dose." Amounts effective for this use will depend on, e.g., the inhibitor composition, the manner of administration, the stage and severity of the disease being treated, the weight and general state of health of the patient, and the judgment of the prescribing physician. Inhibitors of CDK9 activity can be administered chronically or acutely to reduce, inhibit or prevent cartilage degradation and post traumatic osteoarthritis. In certain instances, it will be appropriate to administer an inhibitor of CDK9 activity prophylactically, for instance in subjects at risk of or suspected of developing cartilage degradation and/or post traumatic osteoarthritis.

Alternatively, DNA or RNA that inhibits expression of one or more sequences encoding a CDK9 protein, such as an antisense nucleic acid, a small-interfering nucleic acid (i.e., siRNA), a micro RNA (miRNA), or a nucleic acid that encodes a peptide that blocks expression or activity of a CDK9 can be introduced into patients to achieve inhibition. U.S. Pat. No. 5,580,859 describes the use of injection of naked nucleic acids into cells to obtain expression of the genes which the nucleic acids encode.

Therapeutically effective amounts of CDK9 inhibitor or enhancer compositions of the present invention generally range for the initial administration (that is for therapeutic or prophylactic administration) from about 0.1 µg to about 10 mg of CDK9 inhibitor for a 70 kg patient, usually from about 1.0 µg to about 1 mg, for example, between about 10 µg to about 0.1 mg (100 µg). Typically, lower doses are initially administered and incrementally increased until a desired efficacious dose is reached. These doses can be followed by repeated administrations over weeks to months depending upon the patient's response and condition by evaluating symptoms associated with cartilage degradation and/or post-traumatic osteoarthritis.

For prophylactic use, administration should be given to subjects at risk for or suspected of developing cartilage degradation and/or post-traumatic osteoarthritis. Therapeutic administration may begin concurrently with surgical and/or allograft procedures, and/or as soon as possible after traumatic injury or surgery. This is often followed by repeated administration until at least symptoms are substantially abated and for a period thereafter. In some embodiments, the inhibitor of CDK9 is administered within 10 days, e.g., within 9, 8, 7, 6, 5, 4, 3, 2, 1 days, e.g., within 24, 20, 18, 16, 14, 12, 10, 9, 8, 7, 6, 5, 4, 3, 2, 1 hours after experiencing traumatic injury. In some embodiments, the subject has undergone surgery to repair damaged cartilage tissue. In some embodiments, the subject has received an osteochondral explant, e.g., a cartilage allograft. In some embodiments, the inhibitor of CDK9 is administered concurrently with or prior to surgery. In some embodiments, the inhibitor of CDK9 is administered within 10 days, e.g., within 9, 8, 7, 6, 5, 4, 3, 2, 1 days, e.g., within 24, 20, 18, 16, 14, 12, 10, 9, 8, 7, 6, 5, 4, 3, 2, 1 hours after surgery. In some embodiments, the inhibitor of CDK9 is administered over a course of 10 days, e.g., over 9, 8, 7, 6, 5, 4, 3, 2, 1 days. In various embodiments, the inhibitor of CDK9 is administered every 2 days, every day, or twice daily, as appropriate.

The CDK9 inhibitors for therapeutic or prophylactic treatment are intended for systemic (e.g., parenteral, topical, oral, transdermal) or local (e.g., intralesional) administration. Preferably, the compositions are formulated for oral administration. In certain embodiments, the pharmaceutical compositions are administered parenterally, e.g., intravenously, intranasally, inhalationally, subcutaneously, intradermally, or intramuscularly. Compositions of the invention are also suitable for oral administration. Thus, the invention provides compositions for parenteral administration which comprise a solution of the CDK9 inhibiting agent dissolved or suspended in an acceptable carrier, preferably an aqueous carrier. A variety of aqueous carriers may be used, e.g., water, buffered water, 0.9% saline, 0.3% glycine or another suitable amino acid, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

In embodiments where the CDK9 inhibitor is a small organic compound, the compound (e.g., flavopiridol) and/or an analog thereof can be administered orally, parenterally, (intravenously (IV), intramuscularly (IM), depo-IM, subcutaneously (SQ), and depo-SQ), sublingually, intranasally (inhalation), intrathecally, transdermally (e.g., via transdermal patch), topically, ionophoretically or rectally. Typically the dosage form is selected to facilitate delivery to the brain (e.g., passage through the blood brain barrier). In this context it is noted that the compounds described herein are readily delivered to the brain. Dosage forms known to those of skill in the art are suitable for delivery of the compound.

In varying embodiments, the CDK9 inhibitor is administered intravenously. In embodiments where the CDK9 inhibitor is flavopiridol, dosing can be in accordance with concentrations and scheduling reported in the art. For example, in various embodiments, flavopiridol is administered intravenously in a concentration range of about 10 to about 105 mg/m$^2$ in infusions delivered over 1 to 4 hours, as appropriate. See, e.g., Ramaswamy, et al., *Invest New Drugs*. (2012) 30(2):629-38; Phelps, et al., *Blood*. (2009) 113(12): 2637-45; and Byrd, et al., *Blood*. (2007) 109(2):399-404.

Compositions are provided that contain therapeutically effective amounts of the compound. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

These active agents (e.g.,flavopiridol and/or analogs thereof) can be administered in the "native" form or, if desired, in the form of salts, esters, amides, prodrugs, derivatives, and the like, provided the salt, ester, amide, prodrug or derivative is suitable pharmacologically effective, e.g., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience.

Methods of formulating such derivatives are known to those of skill in the art. For example, the disulfide salts of a number of delivery agents are described in PCT Publication WO 2000/059863 which is incorporated herein by reference. Similarly, acid salts of therapeutic peptides, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, orotic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the pHmax to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments preparation of esters typically involves functionalization of hydroxyl and/or carboxyl groups that are present within the molecular structure of the active agent. In certain embodiments, the esters are typically acyl-substituted derivatives of free alcohol groups, e.g., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

The concentration of CDK9 inhibiting agents of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The CDK9 inhibitors of the invention may also be administered via liposomes, which can be designed to target the conjugates to a particular tissue, for example, cartilage tissue. Liposomes include emulsions, foams, micelles, insoluble monolayers, liquid crystals, phospholipid dispersions, lamellar layers and the like. In these preparations, the peptide, nucleic acid or organic compound to be delivered is incorporated as part of a liposome, alone or in conjunction with a molecule which binds to, e.g., a receptor prevalent among the desired cells, or with other therapeutic compositions. Thus, liposomes filled with a desired peptide, nucleic acid, small molecule or conjugate of the invention can be directed to the damaged or injured lesion, for example, cartilage tissue, joints, injured lesions, where the liposomes then deliver the selected CDK9 inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid liability and stability of the liposomes in the blood stream. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028.

The targeting of liposomes using a variety of targeting agents is well known in the art (see, e.g., U.S. Pat. Nos. 4,957,773 and 4,603,044). For targeting to desired cells, a ligand to be incorporated into the liposome can include, e.g., antibodies or fragments thereof specific for cell surface determinants of the target cells. A liposome suspension containing a CDK9 inhibitor may be administered intravenously, locally (e.g., intralesionally), topically, etc., in a dose which varies according to, inter alia, the manner of administration, the conjugate being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more conjugates of the invention, and more preferably at a concentration of 25%-75%.

For aerosol administration, the inhibitors are preferably supplied in a suitable form along with a surfactant and propellant. Typical percentages of CDK9 inhibitors are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

An effective treatment is indicated by a decrease in observed symptoms (e.g., pain, swelling, joint mobility) as measured according to a clinician or reported by the patient. Alternatively, methods for detecting levels of specific CDK9 activities can be used. Standard assays for detecting CDK9 activity are described herein. Again, an effective treatment is indicated by a substantial reduction in activity of CDK9. As used herein, a "substantial reduction" in CDK9 activity refers to a reduction of at least about 30% in the test sample compared to an untreated control. Preferably, the reduction is at least about 50%, more preferably at least about 75%, and most preferably CDK9 activity levels are reduced by at least about 90% in a sample from a treated mammal compared to an untreated control. In some embodiments, the CDK9 activity is completely inhibited.

5. Matrices Comprising an Inhibitor of CDK9

In various embodiments, the CDK9 inhibitors can be contained within a matrix or a depot. The matrix can serve, in one capacity, as a delivery vehicle for the composition to be delivered to the site of a cartilage lesion or a bone lesion. The matrix also provides a suitable scaffold upon which cartilage repair and regeneration can occur. In one embodiment, the matrix is bioresorbable or biodegradable.

In various embodiments, the matrix can be formed of any material that is suitable for in vivo use, and which provides the characteristics facilitating cartilage repair or bone repair in the presence of an inhibitor of CDK9. The matrix can be formed of materials which include, but are not limited to, synthetic polymers and/or a ground substance. Preferred ground substances include natural polymers and proteoglycans. Natural polymers include, but are not limited to collagen, elastin, reticulin and analogs thereof Proteoglycans include, but are not limited to, any glycosaminoglycan-containing molecules. Particularly preferred glycosaminoglycans include chondroitin sulfate, dermatan sulphate, heparan sulphate, keratan sulphate and hyaluronan. Other preferred ground substances include, but are not limited to, type I collagen, type II collagen, type III collagen, type IV collagen and hyaluronic acid. Preferred synthetic polymers include poly(lactic acid) and poly(glycolic acid).

In one embodiment of the present invention, the matrix includes collagen. For example, the matrix can contain from about 20% to about 100% collagen by dry weight of the matrix, for example, from about 50% to about 100% collagen by dry weight of the matrix, for example, from about 75% to about 100% collagen by dry weight of the matrix.

A matrix suitable for use with the inhibitors of CDK9 can include materials in any suitable form for use in repairing a cartilage lesion or a bone lesion, including a sponge, a membrane, a film or a gel. In one embodiment, a suitable repair matrix includes demineralized bone matrix, synthetic bone graft substitute, autograft tissue, allograft tissue and/or xenograft tissue. In some embodiments, the matrix is formulated for use as a bone graft, for example, as a spinal graft.

Suitable methods for associating an inhibitor of CDK9 with a matrix include any method which allows the inhibitors to be delivered to a site of cartilage repair or bone repair together with the matrix such that the cartilage repair or bone repair product is effective to repair and/or regenerate cartilage or bone at the site. Such methods of association include, but are not limited to, suspension of the composition within the matrix, freeze-drying of the composition onto a surface of the matrix and suspension within the matrix of a carrier/delivery formulation containing the composition. Additionally, the inhibitors of CDK9 can be associated with the matrix prior to placement of the product into a cartilage lesion (i.e., the association of the composition with matrix occurs ex vivo) or alternatively, the matrix can first be implanted into a lesion, followed by association of the inhibitors of CDK9 with the matrix, such as by injection into or on top of the matrix (i.e., the association of the composition with matrix occurs in vivo).

The inhibitors of CDK9 can contain additional delivery formulations or carriers which enhance the association of the composition with the matrix, which enhance the delivery of the composition to the appropriate cells and tissue at the site of the lesion, and which assist in controlling the release of the factors in the composition at the site of the lesion. Suitable delivery formulations include carriers, which, as used herein, include compounds that increase the half-life of a cartilage-inducing composition in the treated animal. Suitable carriers include, but are not limited to, polymeric controlled release vehicles, biodegradable implants, liposomes, bacteria, viruses, oils, cells, esters, and glycols. Preferably, the matrices are bioresorbable or biodegradable.

The inhibitors of CDK9 are present in the matrix at a concentration that is effective to induce, at the site of a cartilage lesion or a bone lesion, one or more of: cellular infiltration, cellular proliferation, angiogenesis, and cellular differentiation to type II collagen-producing chondrocytes. Preferably, the inhibitors of CDK9 are present in the matrices at a concentration that is effective to induce cartilage repair and/or regeneration at the site of a cartilage lesion or a bone lesion. One of skill in the art will be able to adjust the concentration of proteins and/or nucleic acid molecules in the composition depending on the types and number of proteins to be provided by the composition, and the delivery vehicle used.

The matrices can also contain one or more substances that non-covalently attach to the inhibitors of CDK9 in the composition and thus, modify the release rate of the growth factor. Such substances include, but are not limited to, any ground substance or other polymeric substance. As used herein, a ground substance is defined as the non-living matrix of connective tissue, which includes natural polymers and proteoglycans. Natural polymers include, but are not limited to collagen, elastin, reticulin and analogs thereof. Proteoglycans include, but are not limited to any glycosaminoglycan-containing molecules, and include chondroitin sulfate, dermatan sulphate, heparan sulphate, keratan sulphate and hyaluronan. Preferred ground substances include, but are not limited to, type I collagen, type II collagen, type III collagen, type IV collagen and hyaluronic acid. Preferred other polymeric substances include, but are not limited to, poly(lactic acid) and poly(glycolic acid).

In a further embodiment, the matrices can include one or more types of cells which are provided to further enhance chondrogenesis at the site of the cartilage lesion. Such cells include, but are not limited to, fibrochondrocytes, chondrocytes, mesenchymal precursors, and any other cell that can serve as a chondrocyte precursor. Such cells can be associated with the composition and the matrix by any of the methods described above.

In some aspects of the present invention, matrices comprising the inhibitors of CDK9 further comprise at least one bone matrix protein. As used herein, "bone matrix proteins" are any of a group of proteins known in the art to be a component of or associated with the minute collagenous fibers and ground substances which form bone matrix. In various embodiments, the matrices comprise a bone matrix protein that is a member of the TGF-β superfamily, a growth factor protein and/or Cartilage Oligomeric Matrix Protein (COMP). Bone matrix proteins can also include, but are not limited to, osteocalcin, osteonectin, bone sialoprotein (BSP), lysyloxidase, cathepsin L pre, osteopontin, matrix GLA protein (MGP), biglycan, decorin, proteoglycan-chondroitin sulfate III (PG-CS III), bone acidic glycoprotein (BAG-75), thrombospondin (TSP) and/or fibronectin. Preferably, bone matrix proteins suitable for use with the product of the present invention include one or more of: osteocalcin, osteonectin, MGP, TSP, BSP, lysyloxidase and cathepsin L pre. In one embodiment, the at least one bone matrix protein includes at least osteocalcin, osteonectin, BSP, lysyloxidase and cathepsin L pre. A particularly preferred bone matrix protein is MGP, and more preferred is osteonectin, and most preferred is TSP.

The matrices comprising the inhibitors of CDK9 are useful for repairing a variety of defects in cartilage, including both tears and segmental defects in both vascular and avascular cartilage tissue. The product is particularly useful for repairing defects in hyaline (e.g., articular) and/or fibrocartilage (e.g., meniscal). For example, matrices comprising inhibitors of CDK9 find use promoting repair of a meniscal radial tear; a meniscal triple bucket handle tear; a longitudinal tear in the avascular area of a meniscus; or a meniscal segmental lesion.

Because cartilage defects and bone defects (i.e., lesions) can occur in a variety of shapes, sizes, and locations, a matrix comprising the inhibitors of CDK9 is of a shape and size sufficient to conform to a specific defect in the cartilage or the bone of the patient to be treated. Preferably, the matrix, when used in the repair of a cartilage defect or bone defect, achieves a geometry at the defect site that is suitable to provide a therapeutic benefit to the patient. Such a therapeutic benefit can be any improvement in a patient's health and well-being that is related to a correction of the cartilage defect or the bone defect, and preferably, the therapeutic benefit includes the repair of the defect such that the natural configuration of the cartilage or the bone is at least partially restored. The matrix can be fixed or implanted directly into a cartilage lesion or a bone lesion.

6. Compositions and Kits

In a related aspect, the invention provides compositions comprising an osteochondral explant (e.g., ex vivo cartilage tissue) and/or chondrocytes in a solution comprising an inhibitor of cyclin-dependent kinase 9 (CDK9). In some embodiments, the osteochondral explant is allograft cartilage. In some embodiments, the inhibitor of CDK9 is a small organic compound, as described above. In varying embodiments, the inhibitor of CDK9 is flavopiridol, or analogs and salts thereof. In some embodiments, the osteochondral explant is submerged in the solution comprising the inhibitor of CDK9. In varying embodiments, the solution is an aqueous solution, e.g., a physiologically isotonic solution. In some embodiments, the solution comprises flavopiridol at a concentration in the range of about 100 nM to about 1000 nM, e.g., about 300 nM. The solution may contain additional pharmaceutically acceptable excipients, described herein. In some embodiments, the composition is provided as a packaged kit.

EXAMPLES

The following examples are offered to illustrate, but not to limit the claimed invention.

Example 1

CDK9 Inhibition Protects Cartilage from the Catabolic Effects of Pro-Inflammatory Cytokines Methods Human articular chondrocytes—Primary chondrocytes were isolated from cartilage tissues obtained from total knee arthroplasty according to IRB approved protocol and cultured as monolayer (Li et al., *Osteoarthritis Cartilage*. (2011) 19(10):1246-53). The chondrocytes were used for experiments within 3-5 days without passaging to avoid dedifferentiation.

Treatments of chondrocytes—Primary chondrocytes grown in 6-well plates (~80% confluence) were treated with 10 ng/ml lipopolysaccharide (LPS) (Sigma), or 10 ng/ml IL-1β (R&D System) for 5 hours, with or without 300 nM CDK9 inhibitor flavopiridol (Sigma). The cells were washed 3 times with PBS and harvested for RNA extraction.

Quantitative real-time PCR—Total RNA were extracted using the RNeasy Mini Kit (Qiagen) and reverse transcribed using a Superscript first-strand kit (Invitrogen). RT-PCR was performed in triplicates using a 7900HT real-time PCR system (Applied Biosystem) with gene specific probes (Applied Biosystem) and normalized to 18s rRNA, or alternatively, with the PCR Arrays for Human NFκB Signaling Targets (Qiagen, cat. no. 330231), according to the manufacturers' protocol. PCR array data were analyzed by the accompanying online analysis software provided by Qiagen on the internet at qiagen.com.

Assessment of cartilage degradation—Human cartilage explants (about 3 mm cubes) were treated with 1 ng/ml IL-1b for 6 days, in the presence or absence of 6 or 300 nM Flavopiridol (with media change on day 3). The amount of glycosaminoglycan (GAG) released into the media was determined by the colorimetric dimethylmethylene blue dye-assay, with chondroitin sulfate as standard (Farndale, et al., *Biochim Biophys Acta* 883:173-177). The release of Col2a degradation products into the media was determined by measuring the amount of cleaved Col2a peptides (Poole, et al., *J Immunol Methods* (2004) 294:145-153.) with the C2C ELISA kit (IBEX Pharmaceuticals) according to the manufacturer's protocol.

Statistical analysis—Values of all measurements were expressed as the mean+standard deviation. Statistical comparison was performed by two-tailed Student's t test. Values of $p<0.05\%$ were considered significant.

Results

Flavopiridol inhibits LPS-induced inflammatory response in chondrocytes. To test whether CDK9 inhibitor flavopiridol inhibits the transcriptional activation of primary inflammatory response genes, human articular chondrocytes were treated with LPS for 5 hours. As expected, this activated transcription of the primary response genes IL-1β and iNOS (FIG. 1). However, pre-treatment with 300 nM flavopiridol strongly attenuated the transcriptional activation of both genes. Importantly, addition of flavopiridol 3 hours after LPS treatment still markedly inhibited IL-1β and iNOS activation (FIG. 1).

Figure 2:
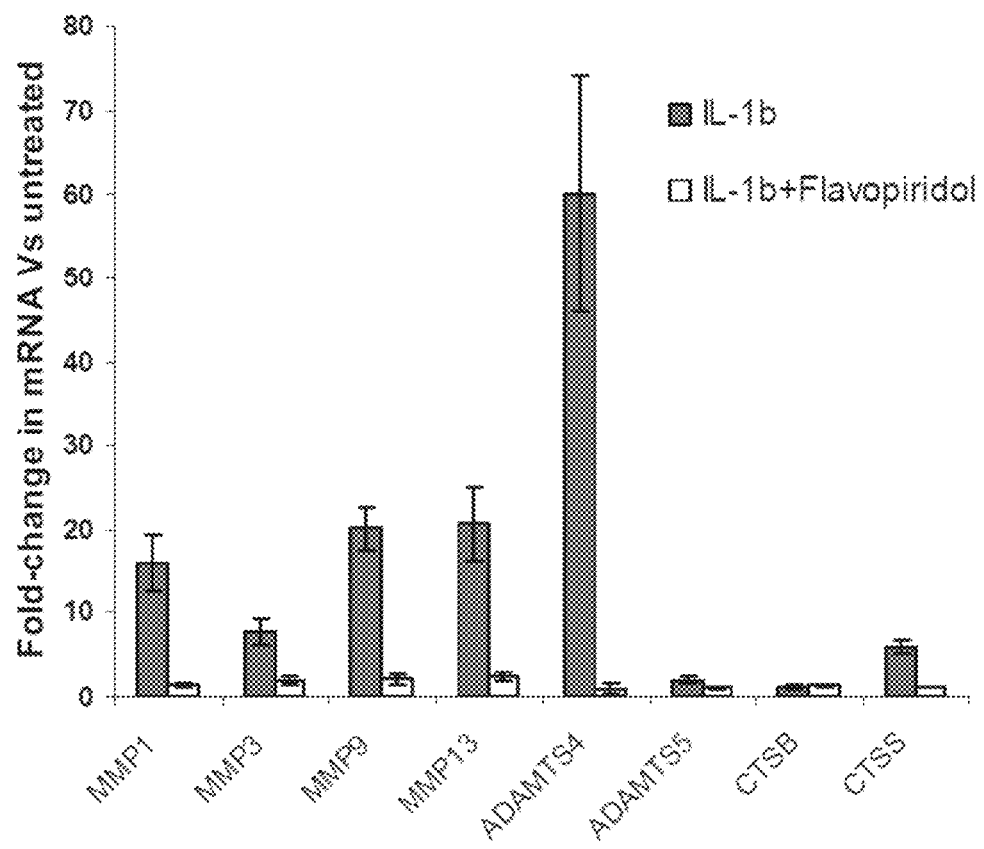
FIG. 2 illustrates that flavopiridol inhibits IL-1β-induced expression of matrix-degrading enzymes in chondrocytes.

Flavopiridol prevents IL-1β-induced expression of matrix-degrading enzymes in chondrocytes. IL-1β induces a host of MMPs and ADAMTSs that degrade collagen and aggrecan, respectively, in cartilage matrix. We tested whether CDK9 inhibition could effectively suppress this in chondrocytes. Upon IL-1β stimulation, the expression of MMPs and ADAMTSs were activated as expected. However, co-treatment with flavopiridol effectively suppressed the activation of these genes (FIG. 2) (except cathepsin B (CTSB), which was not activated by IL-1β). These data indicate that CDK9 activity is important for the activation of cartilage-degrading enzymes following inflammatory stimulation.

Figure 3:
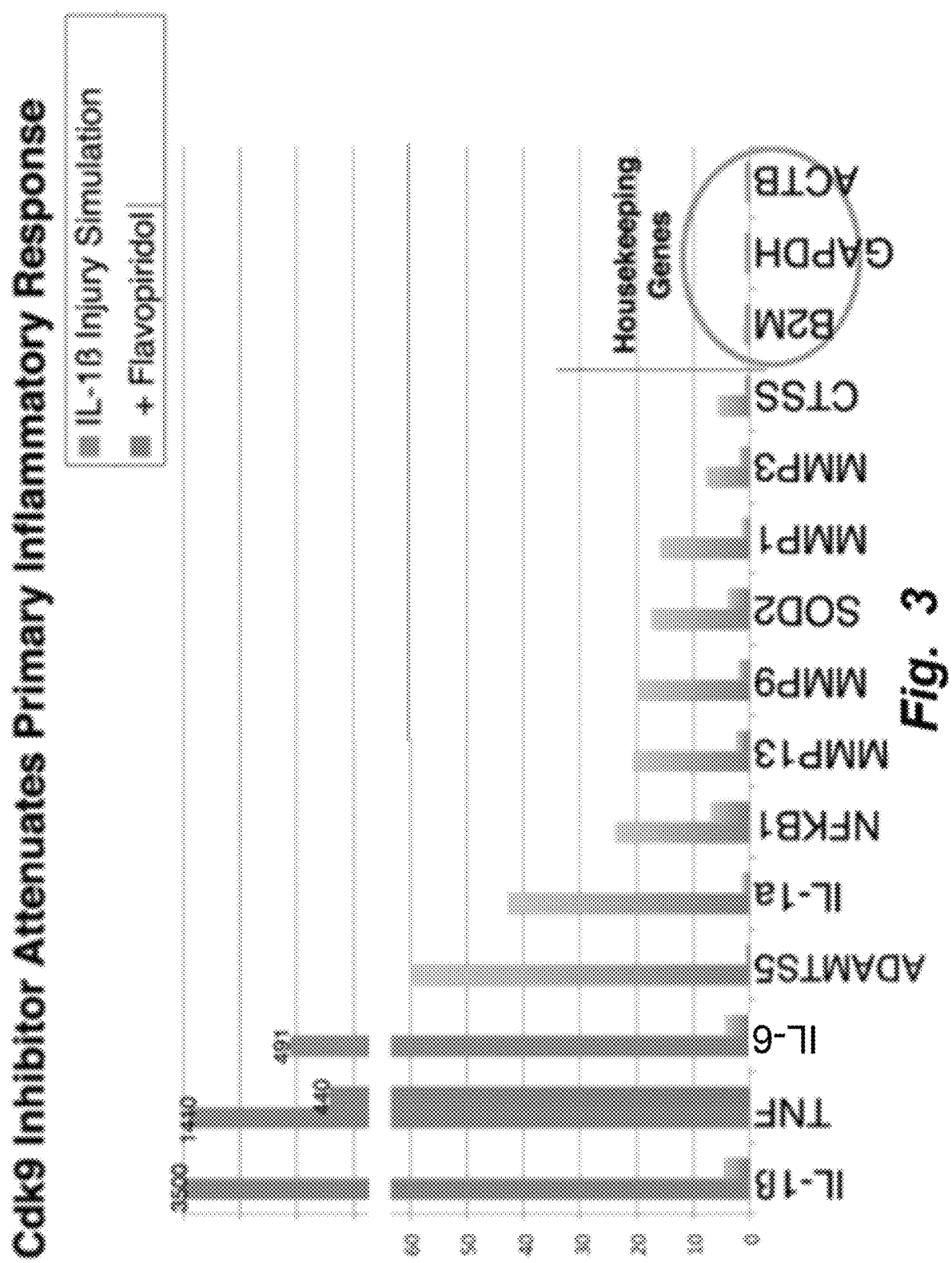
FIG. 3 illustrates that inhibition of CDK9 by flavopiridol effectively suppresses the activation of a broad range of primary inflammatory response genes by IL-1β. Primary human chondrocytes from 3 donors were treated with IL-1β with or without cdk9 inhibitor (300 nM flavopiridol). Gene expression was analyzed using PCR-Array for NFκB targets (Qiagen) on a HT-7900 instrument. IL-1β strongly activated the primary response genes. Inhibition of cdk9 activity almost completely abolishes the effects of IL-1β. For example, IL-1β induced expression of IL-6 by 492-fold, but only 4.2-fold in the presence of cdk9 inhibitor, representing a 99.2% repression of IL-1β-dependent inflammatory response gene transcription. On average, across 3 donors, cdk9 inhibition repressed IL-1β activity by >86%, with respect to 54 inflammatory response genes. Importantly, housekeeping genes are unaffected by either IL-1β or cdk9 inhibitors.

Flavopiridol suppresses a broad range of primary inflammatory response genes. We next tested the effectiveness of flavopiridol in inhibiting the IL-1β-mediated activation of multiple primary inflammatory response genes in chondrocytes, using a NF-κB target PCR array (SABiosciences). As shown in FIG. 3, IL-1β strongly activated many NF-κB-dependent primary response genes (presented as fold-induction over untreated control on a logarithmic scale, in the absence (blue bars) or presence (red bars) of flavopiridol. The percent inhibition by flavopiridol was shown on top of each bars). In most cases, flavopiridol effectively abolished the activation (>90%) of these genes. For example, IL-1β activated IL-6 by 492-fold, but only 4.1-fold in the presence of flavopiridol. Importantly, housekeeping genes are largely unaffected by either IL-1β or flavopiridol.

Figure 4A:
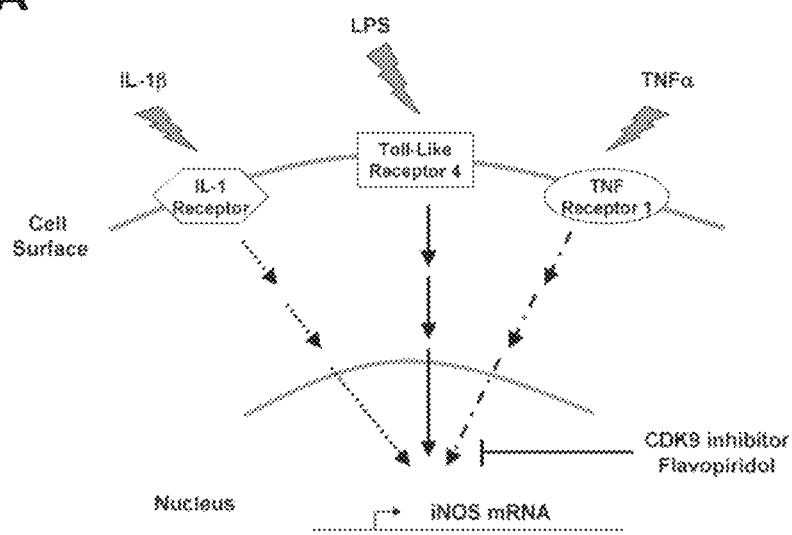
FIG. 4A illustrates that the CDK9 inhibitor flavopiridol is effective against different inflammatory stimuli.
Figure 4B:
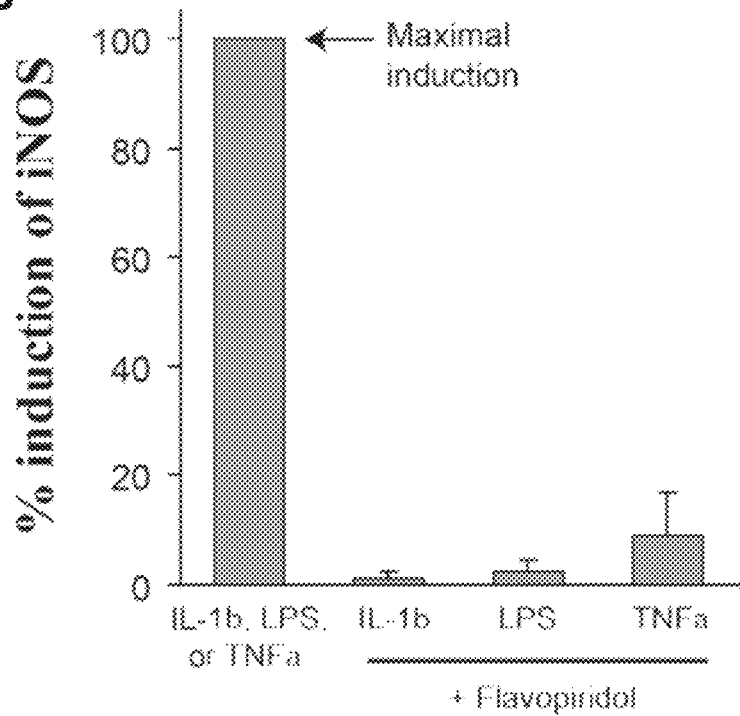
FIG. 4B shows data of primary_human articular chondrocytes (n=3 donors) in monolayer culture were treated with different inflammatory stimuli (10 ng/ml of either IL-1β, LPS, or TNFα) with or without 300 nM Flavopiridol for 5 hours. iNOS mRNA was quantified by real-time PCR as a measure of inflammatory response. The induction of iNOS by each stimulus alone was arbitrarily set to 100% (first bar) and compared to the respective value obtained in sample co-treated with each inflammatory stimulus and Flavopiridol.

CDK9 controls the activation of inflammatory response from diverse signals. Although the rate-limiting step for transcriptional activation of inflammatory response genes in lymphocytes is controlled by CDK9 (Hargreaves et al., *Cell.* (2009) 138(1):129-45; Zippo, et al., *Cell* (2009) 138:1122-36), its role in regulating the innate inflammatory response in articular chondrocytes has not been investigated. To this end, we tested the involvement of CDK9 in the activation of inflammatory response genes in chondrocytes simulated by three different inflammatory signals; namely, Interleukin 1 beta (IL-1β), Lipopolysaccharides (LPS), and Tissue Necrosis Factor alpha (TNFα). Cellular response to IL-1β, LPS, or TNFα is mediated by three distinct pathways—activation of the IL-1Receptor, Toll-Like Receptor 4, or TNF Receptor 1, respectively (FIG. 4A). Chondrocytes were treated with the above three agents independently, in the presence or absence of the CDK9 inhibitor Flavopiridol. The mRNA expression of the inducible nitric oxide synthase (iNOS) (Maier et al., *Biochim Biophys Acta.* (1994) 1208(1):145-50), a common effector gene for all three pathways, was then determined to assess the immune response in chondrocytes. The results showed that Flavopiridol greatly suppressed the activation of iNOS expression in all three pathways (FIG. 4B), demonstrating the effectiveness and versatility of Flavopiridol in preventing inflammatory response from diverse signals. Thus our data confirmed previous finding in other systems and established CDK9 as a central regulatory point for innate inflammatory response in chondrocytes.

Figure 5:
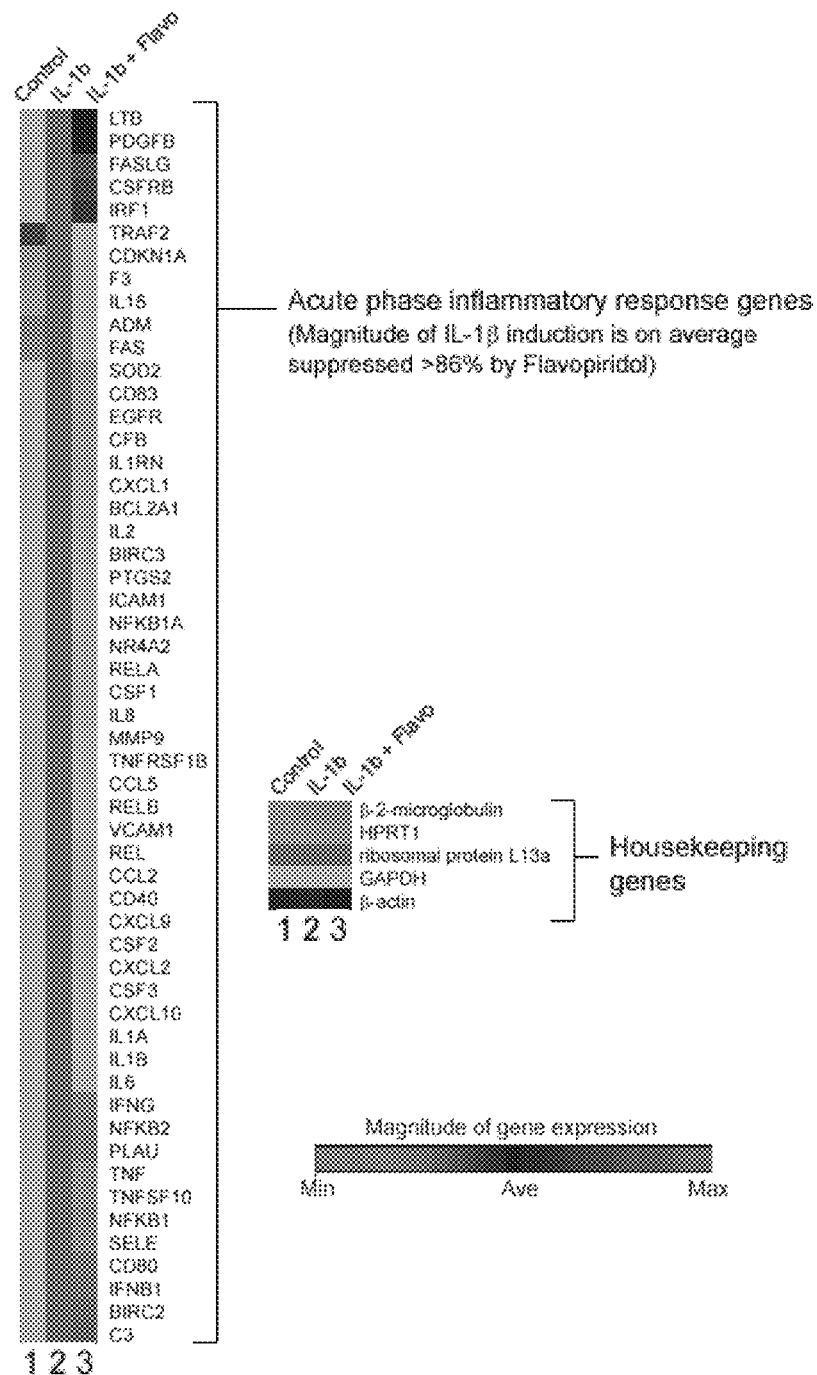
FIG. 5 illustrates that flavopiridol effectively suppresses the induction of a broad range of inflammatory mediators. Primary human chondrocytes (n=3) in monolayer culture were treated with 10 ng/ml IL-1β with or without 300 nM Flavopiridol for 5 hours. Gene expression was analyzed using real-time PCR-Array for NFκB targets (Qiagen) as described in Methods and shown here as heat map (Green=minimum expression, Red=maximum expression). Listed are 54 out of 60 NFκB-targeted genes tested that were induced >2-fold by IL-1β, which strongly activated these genes (compare lanes 1 and 2). Flavopiridol almost completely abolishes the effects of IL-1β (lane 3). Importantly, housekeeping genes are unaffected by either IL-1β or Flavopiridol.

CDK9 inhibition prevents the activation of a broad spectrum of inflammatory response genes. To further investigate the effects of CDK9 inhibition on the activation of other inflammatory mediators besides iNOS, the gene expression profiles of chondrocytes treated with IL-1β for 5 hrs were determined by real-time PCR arrays. Each PCR array contained 84 key genes responsive to NFκB signal transduction (Qiagen), which regulates multiple cellular processes such as inflammatory, immunity, and stress responses. The average gene expression profiles from three chondrocyte donors were presented as heat maps, in which low and high relative expressions were represented by green and red colors, respectively (FIG. 5). The results showed that IL-1β strongly activated the majority of these NFκB-target genes (FIG. 5, compared lane 1& 2), while CDK9 inhibition by Flavopiridol almost completely abolished the effects of IL-1β (lane 3). On average, across three chondrocyte donors, CDK9 inhibition repressed IL-1β activity by >86%, with respect to 54 out of 60 NFκB-target genes (listed in FIG. 5) that were activated by at least 2-fold under out experimental conditions. Importantly, housekeeping genes were not affected by either IL-1β or Flavopiridol. These data demonstrated that CDK9 can be targeted to effectively suppress the activation of a cascade of downstream inflammatory response genes.

CDK9 inhibition prevents the activation of catabolic genes in chondrocytes. Besides activating the acute phase inflammatory genes, pro-inflammatory cytokines such as IL-1β and TNFα can also stimulate the expression of catabolic genes in chondrocytes (Goldring, et al., *Ann Rheum Dis* (2008) 67 Suppl 3:iii75-82; Kobayashi, et al., *Arthritis Rheum* (2005) 52:128-135). These catabolic genes include the various MMPs and ADAMTS4 (aggrecanase) that degrade the cartilage matrix. Given the role of CDK9 in activation of inflammatory genes, we next examined the effects of CDK9 inhibition in the induction of MMPs and ADAMTS4 in chondrocytes treated with IL-1β. The results showed that IL-1β-mediated up-regulation of MMP1, 3, 9, and 13, as well as ADAMTS4 mRNAs was markedly suppressed by co-treatment with Flavopiridol. These data indicated that CDK9 inhibition prevents the activation of catabolic genes in chondrocytes.

Figure 8:
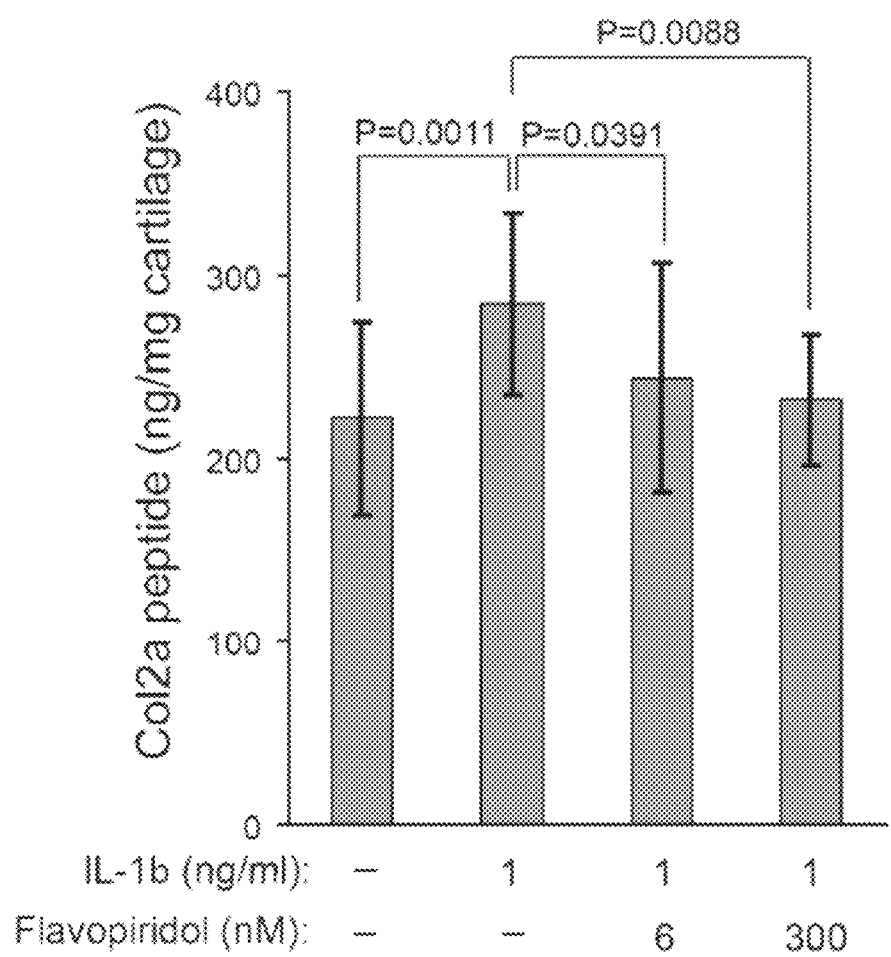
FIG. 8 illustrates CDK9 inhibition prevents IL-1β-induced Col2a breakdown in cartilage. Human cartilage explants (n=5) were treated with 1 ng/ml IL-1β and the indicated concentrations of Flavopiridol for 6 days (media change at day 3). Cleaved Col2a peptides released into the medium was measured by C2C ELISA and normalized to the wet weight of the explants as described in the Methods. Treatment with IL-1β alone caused cartilage degradation as indicated by increased Col2a peptides. In the presence of Flavopiridol, Col2a peptides release returned to baseline.
Figure 9:
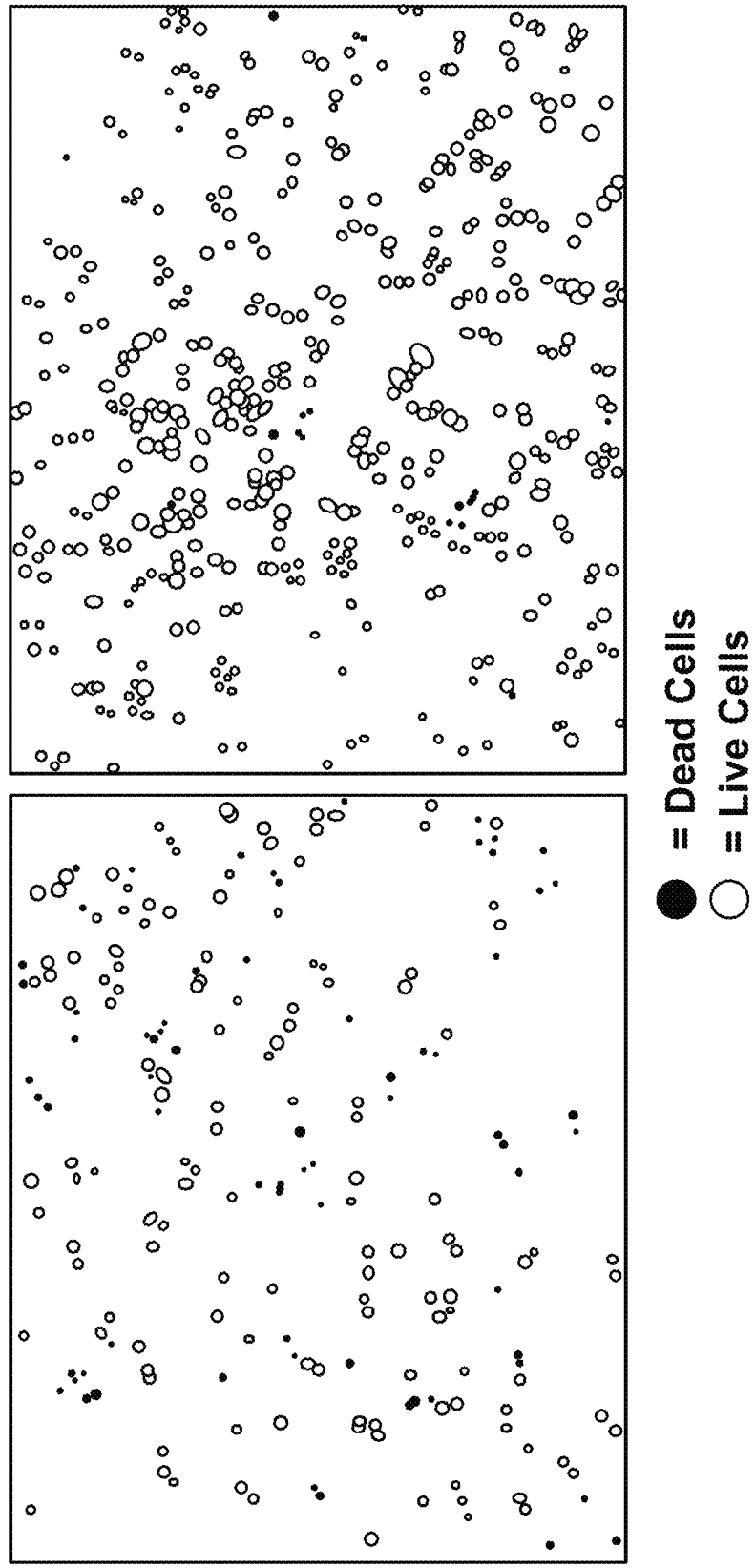
FIG. 9 illustrates that inhibition of CDK9 with flavopiridol strongly reduced the number of dead or dying cells in the cartilage explants after simulated injury with IL-1β. Human cartilage explants were treated with IL-1β to simulate injury, with or without CDK9 inhibitor. Cell death was measured with a live/dead stain.

CDK9 inhibition protects cartilage from the catabolic effects of IL-1β. Since CDK9 inhibition suppresses activation of inflammatory and catabolic genes in chondrocytes, we next determined whether Flavopiridol can protect cartilage from the deleterious effects of pro-inflammatory cytokines. To this end, cartilage explants were isolated and cultured in media containing 1 ng/mL IL-1β, in the presence or absence of Flavopiridol for 6 days. Degradation of cartilage matrix was assessed by measuring the release of GAG and Col2a cleavage peptides into the culturing media. As expected, IL-1β alone increased the amount of both GAG (FIG. 7) and Col2a peptides (FIG. 8) released into the media (compared first and second bars). However, the concentrations of both GAG and Col2a peptides were reduced by 6 nM Flavopiridol and returned to baseline levels by 300 nM Flavopiridol (FIGS. 7 and 8). Thus our data provided evidence that CDK9 inhibition prevented the catabolic destruction of cartilage by IL-1β.

Discussion

The etiology of primary OA remains incompletely understood and the involvement of inflammation is controversy. However, it is well-established that damage to Col2a originates around chondrocytes at the cartilage matrix surface (Hollander, et al., *J Clin Invest* (1995) 96:2859-2869.). Since inflammatory response induces chondrocyte apoptosis and cartilage matrix breakdown (Goldring, et al., *Ann Rheum Dis* (2008) 67 Suppl 3:iii75-82), there are several anti-OA strategies that target either specific branches of the inflammatory signaling cascade (e.g. IL-1, IL-6, TNFα, and NFκB inhibitors) (Kobayashi, et al., *Arthritis Rheum* (2005) 52:128-135; Attur, et al., *Osteoarthritis Cartilage* (2011) 19:1158-1164; Attur, et al., *J Biol Chem* (2000) 275:40307-40315), or the downstream events such as apoptosis with caspase inhibitors (Lotz, et al., *Arthritis Res Ther*. (2007) 12:211). However, because inflammation can be induced by a variety of stimuli, the above individual approaches would have limited effectiveness in handling the diverse challenges in a biological system, as well as limited abilities in efficiently suppressing a broad range of inflammatory mediator expression. Our novel and unique approach to solving this problem is to directly target CDK9 that activates transcription of primary inflammatory response genes. Using the pharmacological CDK9 inhibitor Flavopiridol, we have shown cartilage can be protected from the harmful effects of pro-inflammatory cytokines.

Figure 6:
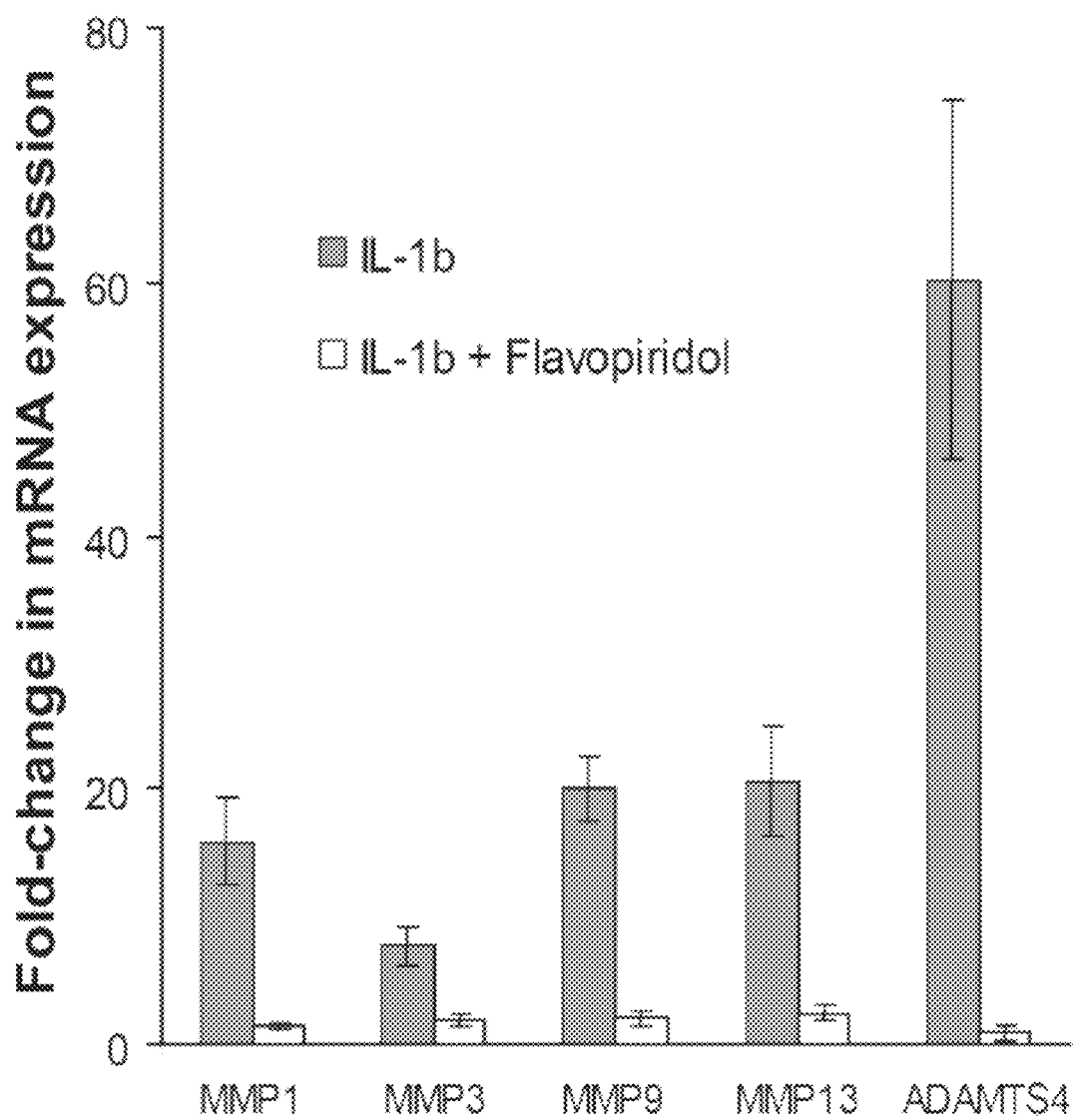
FIG. 6 illustrates that CDK9 inhibition prevents IL-1β-induced MMPs and ADAMTS4 expression. Primary chondrocytes (n=3) were treated with 10 ng/ml IL-1β with or without Flavopiridol for 5 hours, and the mRNA expression of cartilage degrading enzymes MMP-1,-3,-9,-13, and ADAMTS4 (aggrecanase) was determined by real-time PCR as described in Methods.

Our results demonstrate for the first time in chondrocytes that Flavopiridol effectively suppress the innate immune response to multiple inflammatory stimuli (FIG. 4), and prevented the induction of a host of inflammatory mediators (FIG. 5), as well as MMPs and aggrecanase that degrade the cartilage matrix (FIG. 6). In most cases, Flavopiridol almost completely abolishes the activation of inflammatory mediator expression. For example, from the PCR array data (FIG. 2), IL-1β induced expression of IL-6 by 492-fold, but only 4.2-fold in the presence of Flavopiridol, representing a 99.2% repression of IL-1B-dependent inflammatory response gene transcription. These data are further supported by our observation that less IL-1β-induced matrix degradation products of GAG and Col2a is detected in cartilage explants treated with Flavopiridol (FIGS. 7 and 8). The reduction in matrix degradation products is not due to the loss of cell viability in cartilage treated with Flavopiridol, because live/dead staining revealed similar chondrocyte viabilities between control and Flavopiridol treated cartilage.

Flavopiridol is an ATP analog that selectively inhibits CDK9 kinase activity by a high affinity interaction with its ATP-binding pocket (Ni, et al., *PLoS One*. (2010) 5(11):e13792). Flavopiridol was originally known for its anti-proliferation properties by suppressing cell-cycle progression. Its pharmacological activity is well-documented over the last two decades because of its use in clinical trials as anti-proliferation/cancer agent (reviewed by Wang and Ren, *Mini Rev Med Chem*. (2010) 10(11):1058-70). Taken advantage of the anti-proliferative effects of Flavopiridol, Sekine et al have demonstrated that systemic administration of Flavopiridol reduced synovial hyperplasia and prevented rheumatoid arthritis (RA) in a collagen-induced mouse model (Sekine et al., *J Immunol*. (2008) 180(3):1954-61). However, we believed the anti-RA activity of Flavopiridol is likely due to the systematic suppression of B-cell-mediated immune response to the injected collagen, rather than the localized suppression of the innate immune response in cartilage. Our group has developed a non-invasive post-traumatic OA (PTOA) model in mouse (Christiansen et al., *Osteoarthritis Cartilage*. (2012) 20(7):773-82) useful for testing the ability of Flavopiridol and other CDK9 inhibitors to prevent OA, optionally in conjunction with other existing PTOA models.

In summary, our data for the first time demonstrate the absolute requirement of CDK9 activity in the activation of primary inflammatory response genes in human chondrocytes. In addition, our results strongly indicate that Flavopiridol is an effective and versatile agent to prevent activation of acute inflammatory response and catabolic pathways in cartilage. The present data show the effectiveness of flavopiridol in suppressing an inflammatory response in chondrocytes, and thus its therapeutic implications in preventing cartilage breakdown in joint injuries, or in osteochondral explants. CDK9 inhibitors thus provide a new strategy to prevent or delay the onset of OA.

Example 2

CDK9 Inhibition Prevents or Delays the Onset of Long-Term Post-Traumatic Osteoarthritis (PTOA)

Our model of mouse knee injury consistently causes PTOA within 8 weeks. Injured and uninjured mice will be treated with either CDK9 inhibitor or saline control. Treatment with CDK9 inhibitor will be initiated early after joint injury, and maintained for the duration of maximal primary response gene activation. The treatment duration should not exceed 7 days post-injury. (A) the long-term development of PTOA, (B) the level of serum OA biomarkers, and (C) the changes in subchondral bone microstructure by micro-computed tomography (μCT) are measured.

Currently accepted mouse models of PTOA rely on non-physiological methods to induce OA, including using a needle to induce cruciate transection in a 'closed knee', damaging knee ligaments using 'open knee' surgical techniques (Glasson, et al., *Nature*, (2005) 434(7033): 644-8; Kamekura, et al., Osteoarthritis and cartilage/OARS, *Osteoarthritis Research Society*, (2005) 13(7): 632-41; Glasson, et al., Osteoarthritis and cartilage/OARS, Osteoarthritis Research Society, (2007) 15(9): 1061-9), applying repeated bouts of supraphysiological mechanical loads (Poulet, et al., *Arthritis & Rheumatism*, (2011) 63(1): 137-147), and directly injecting collagenase (van Osch, et al., *The Journal of Rheumatology*, (1996) 23(7): 1227-32; Joosten, et al., *Am J Pathol*, (2004) 165(3): 959-67) or chemical agents such as iodoacetate (Ameye, et al., *Curr Opin Rheumatol*, (2006) 18(5): 537-47) into the joint space. While these existing models all initiate OA, they are invasive and non-physiological and do not faithfully mimic the common low-energy human knee traumas such as ACL tears. In addition, the invasive nature of the surgical procedures is likely to initiate an inflammatory response of its own, obfuscating studies of the natural course of the inflammatory response associated with an ACL tear.

We have developed a whole-joint injury model to initiate post-traumatic OA in mice, in which a single rapid non-invasive mechanical load induces ACL rupture. This model faithfully replicates a clinically relevant human knee injury, enabling us to focus on the natural early events of joint injury that initiate the subsequent progression of OA. Our model represents an advance over other animal models of PTOA, since it is a noninvasive injury that mimics a clinically relevant situation. The injuries are highly reproducible and easy to perform, which enables us to design experiments with more variables and obtain statistically significant results using fewer animals. As with other more invasive PTOA mouse models (Glasson, et al., *Nature*, (2005) 434(7033): 644-8), OA develops consistently within 8-12 weeks of injury. As in human knee injuries, we observe an initial acute inflammatory response and joint swelling that resolves in a few days, and extensive remodeling of subchondral bone and cartilage. Also comparable to human knee injuries (Dahlberg, et al., *AnnRheum Dis*, (1994) 53: 823-7), we observe a systemic inflammatory response that results in similar (although lower magnitude) structural changes in the contralateral uninjured knee.

Figure 10:
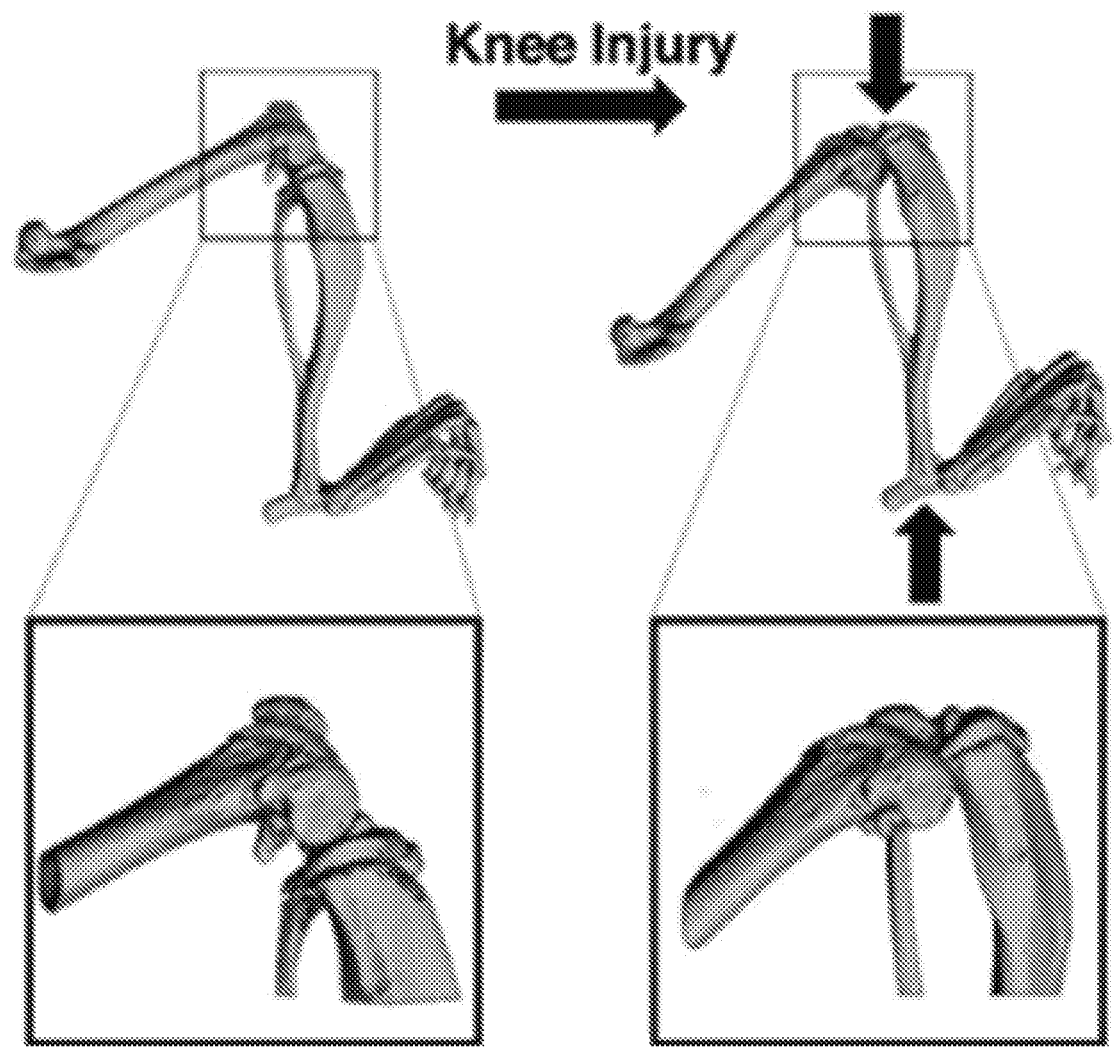
FIG. 10 illustrates application of a whole-joint injury model to initiate post-traumatic OA in mice, in which a single rapid non-invasive mechanical load induces anterior cruciate ligament (ACL) rupture. To generate knee injuries, the mouse is anesthetized using isoflurane inhalation, and then the right leg of each mouse is subjected to tibial compression loading.

To generate knee injuries, the mouse is anesthetized using isoflurane inhalation, and then the right leg of each mouse is subjected to tibial compression loading, as shown in FIG. 10. The tibial compression system consists of two custom-designed loading platens. The bottom platen holds the flexed knee, and the top platen holds the foot with the ankle slightly flexed. The platens are aligned vertically and positioned within an electromagnetic materials testing machine (Bose EnduraTec ElectroForce 3200, Eden Prairie, Minn.). A single axial compressive load, at a loading rate of 1 millimeter per second, is applied to a target compressive load of 12 Newtons (N) to induce the knee injury.

Figure 11A:
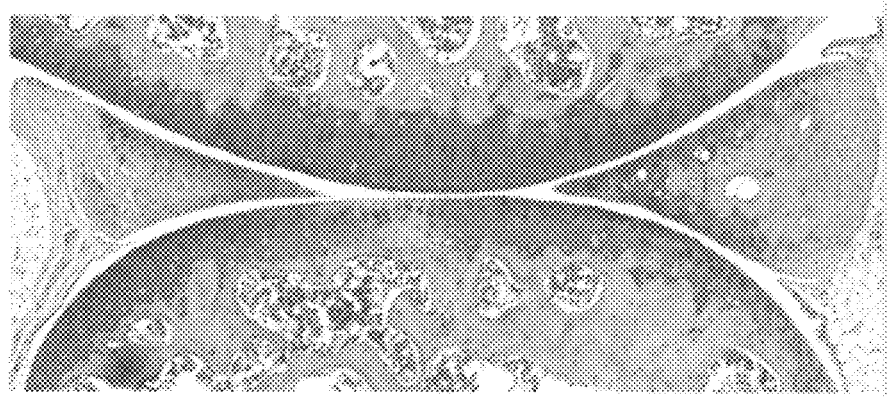
FIG. 11A illustrates a typical histology of an injured joint 8-weeks post surgery and FIG. 11B illustrates a contralateral uninjured joint 8-weeks post-injury. Safranin-O/Fast Green stained mouse knee sections 8-weeks post-injury. A-Uninjured contralateral knee, B-Injured knee. Note the loss of proteoglycans, damaged meniscus, and calcification of the meniscus after injury.
Figure 11B:
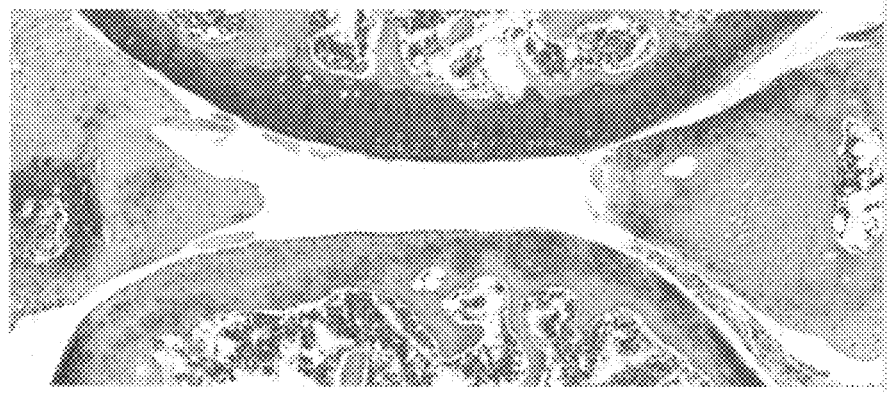
Figure 12:
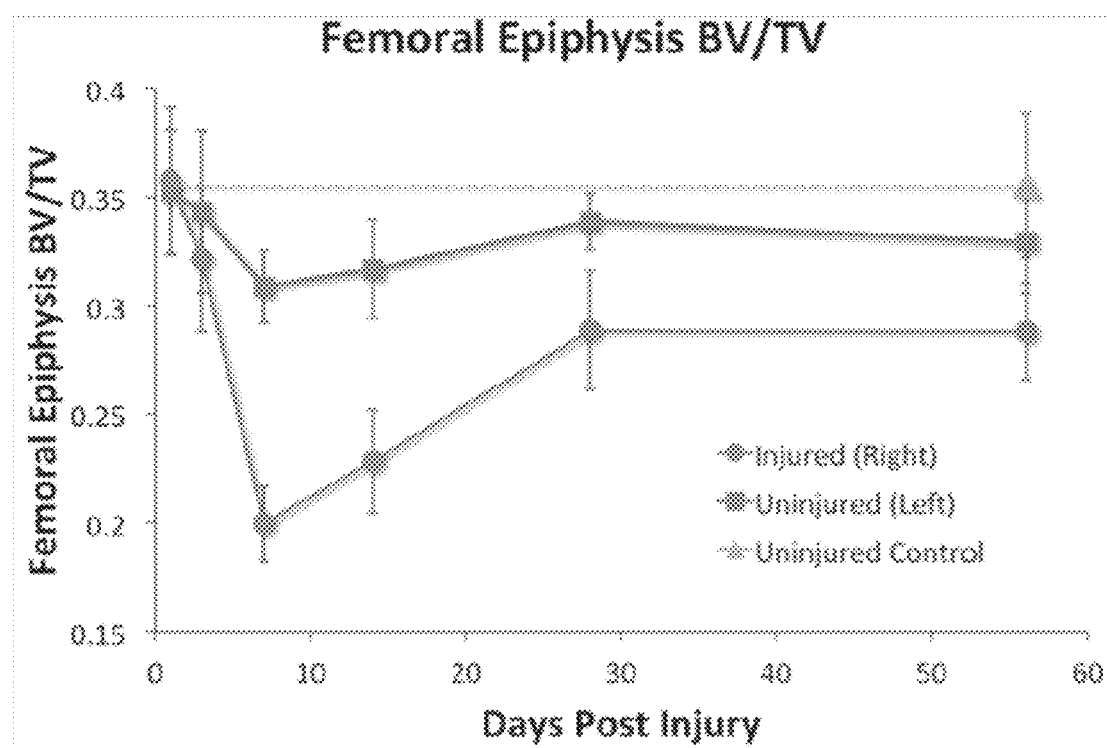
FIG. 12 illustrates quantitative analysis of bone volume in injured and control joints by μCT. Note the rapid and substantial (44%) loss of subchondral bone volume is reproducibly seen in the first few days after injury. Error bars indicate standard deviation, with n=6 for each data point.
Figure 13:
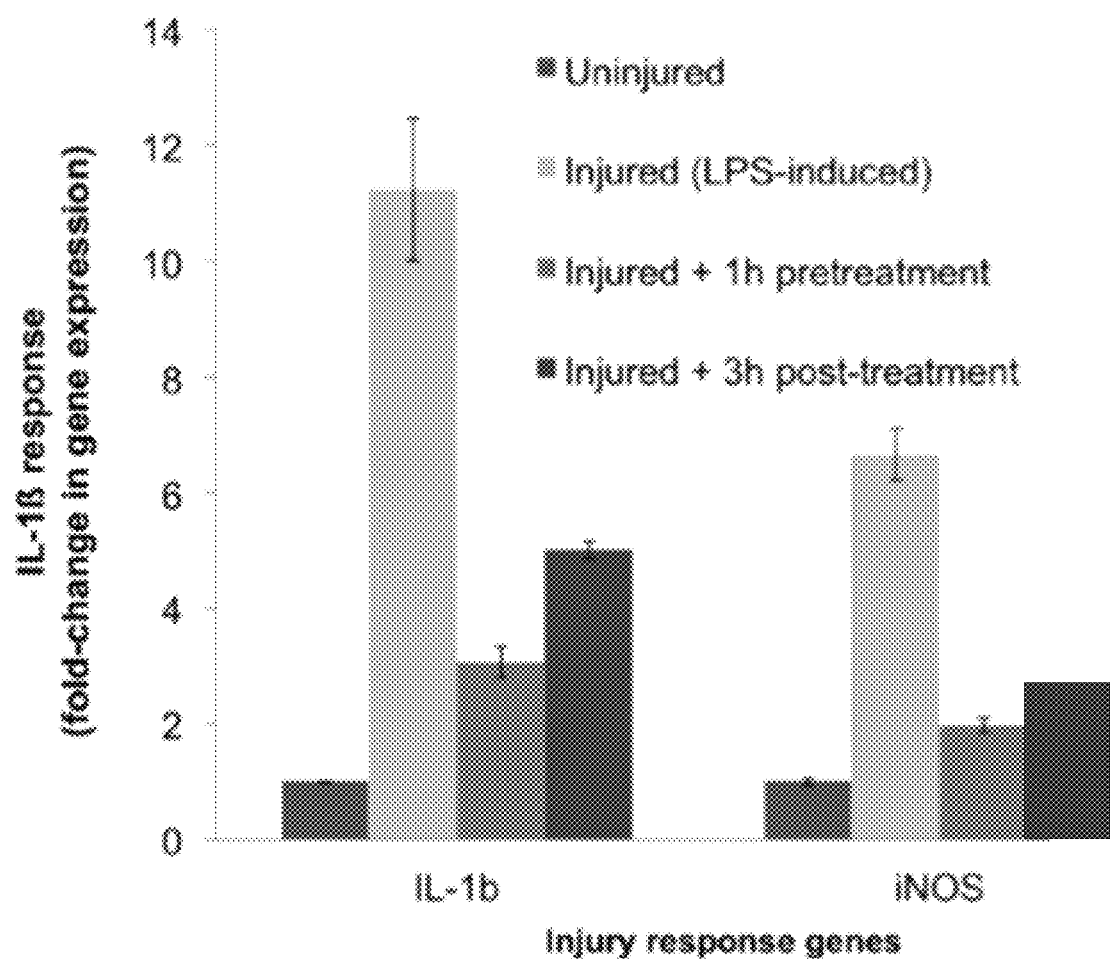
FIG. 13 illustrates Cdk9 Inhibition Treatment Window. Injury was simulated with a strong inflammatory stimulus (10 ng/ml LPS), and iNOS and IL-1β mRNA expression were quantified by TaqMan RT-PCR as a measure of the inflammatory response. Pretreatment with flavopiridol substantially reduced the inflammatory response. Importantly, flavopiridol treatment 3 hours after inflammatory stimulus was also effective, indicating that a treatment window of >3 hours exists.

In this model, joint injury reproducibly occurs at a compressive magnitude between 10N to 11N and is evident by an abrupt change in the force profile, and a visible dislocation of the knee joint. Osteoarthritis consistently develops within 8 weeks. The typical histology of an injured joint and contralateral uninjured joint 8-weeks post-injury is shown in FIG. 11. A significant loss of proteoglycans is observed by 8 weeks, as well as hypertrophy and calcification of the meniscus. Postmortem analysis using high-resolution x-ray microscopy (XRadia, VersaXRM-500, Pleasanton Calif.) and standard micro-computed tomography (SCANCO, µCT 35, Bassersdorf Switzerland) indicated that the ACL was disrupted in all mice examined, typically due to a tibial ACL avulsion fracture. Osteophytes and heterotopic bone formation were present by 8-weeks post-injury, predominantly on the medial and posterior aspects of the joint. Quantitative analysis of bone volume in the µCT images indicated that the injury induced a pronounced initial loss of trabecular bone volume that was evident within 3 days post-injury, shown in FIG. 12. There was maximal bone loss 7 days after injury (40% and 44% loss of trabecular bone volume at the tibial and femoral epiphysis, respectively). The bone volume was slowly regained by week 4, although not to its original value (~80% of the value on day 1). The observation of such rapid remodeling of trabecular bone is novel, and further emphasizes the need for early intervention after joint injury. Analysis of the contralateral uninjured knee revealed similar changes in bone volume, though to a much lesser extent. The observation of a systemic response to the localized injury supports clinical studies which found elevated markers of joint degradation in the uninjured knee of patients with ACL rupture injuries (Dahlberg, et al., *Ann Rheum Dis*, (1994) 53: 823-7).

In summary, we have developed a non-invasive joint injury model in mice that closely mimics clinically relevant human joint injuries. This new injury model is an improvement to existing models, which use non-physiological or invasive methods to create injury, methods that could obfuscate studies of the primary response gene activation.

Our mouse model of joint injury consistently causes PTOA within 8 weeks, and this is in agreement with the many other models of mouse PTOA. Delaying the onset of PTOA to 3 or 4 months in mice would represent a substantial improvement in disease progression. Injured and uninjured mice are treated with either CDK9 inhibitor or saline control. Initial treatment is within 1 to 24 hours of injury, and that the treatment duration does exceed 7 days post-injury. We measure (A) the long-term development of PTOA, (B) serum biomarkers of OA, and (C) changes in subchondral bone microstructure by µCT.

Treatment Groups: Mice are injured as described above, or undergo anesthesia and handling but without receiving joint injury. Injured and uninjured mice will be treated with either CDK9 inhibitor or saline control. Mice are randomly assigned to one of four groups: injured or uninjured, and treated with flavopiridol or vehicle control. Treated mice receive ckd9 inhibitor flavopiridol administered systemically through an IP injection as described by Sekine et al (Sekine, et al., *Journal of Immunology*, (2008) 180(3): 1954-61), and control mice receive vehicle only (0.01% DMSO in saline). Mice are injured as described above, or undergo anesthesia and handling but without receiving joint injury.

Histological Assessment of PTOA. Histology is the standard method to evaluate OA in mice knees. To assess the progression of PTOA in a semi-quantitative manner, the guidelines set forth by the OARSI histopathology initiative late last year are followed (Glasson, et al., Osteoarthritis and cartilage/OARS, *Osteoarthritis Research Society*, (2010) 18 Suppl 3: S17-23, 2010; Aigner, et al., Osteoarthritis and cartilage/OARS, *Osteoarthritis Research Society*, 18 Suppl 3: S2-6). Briefly, mouse knees will be dissected to remove skin and excess muscle and paraffin-embedded. Frontal sections, serially harvested at 80-100 µm increments, are obtained to cover the entire articulating surface. Sections are stained for proteoglycan content using Safranin-O and counterstained with Fast Green. At least 2 trained individuals perform the grading of OA using the recommended scoring system (Glasson, et al., Osteoarthritis and cartilage/OARS, *Osteoarthritis Research Society*, (2010) 18 Suppl 3: S17-23). Evaluators are without any knowledge of the treatment or injury status of the sections. OA scores are compared in across the treatment groups using the JMP 9.0 statistical package.

Serum Biomarkers of OA. Serum biomarkers are promising for monitoring the clinical progression of OA. Most of the serum biomarkers rely on quantifying the breakdown products of matrix components specific to articular cartilage. A few rely on the increased synthesis of collagen-specific proteins, for example the pro-domain of type II collagen that is shed during collagen fibrillogenesis. One of the few serum biomarkers also validated in mouse serum is cartilage oligomeric matrix protein (COMP). The presence of COMP is quantified in the mouse serum, using commercially available kits (MD BioProducts, Zürich Switzerland). Serum levels of COMP will be compared across groups and with time, in combination with the OA scores from above, to determine the efficacy of CDK9 inhibition in preventing PTOA.

MicroCT analysis. Remodeling of subchondral bone, an advancing tidemark with increased calcification of the articular cartilage and meniscus, and osteophyte formation are all hallmarks of osteoarthritis that can be quantified using microCT analysis. Mice will be scanned 1 day before injury, and then again at the indicated time points. An in-vivo micro-computed tomography instrument (SCANCO vivaCT-40, Bassersdorf, Switzerland) will be used, and various aspects of bone microstructure quantified using the included software. Comparisons between groups and across time will be performed to determine the efficacy of CDK9 inhibition in preventing PTOA.

Timecourse: This example focuses on the prevention or delay of PTOA in the long term. OA consistently develops within 2 months in our model. A delay in the onset of OA by 2 additional months is considered an advance in the treatment of mouse PTOA, and holds promise for translation into the clinical setting. PTOA is evaluated at 2, 3, and 4 months post-injury.

REFERENCES

1. Brandt, K. D.; Dieppe, P.; and Radin, E.: Etiopathogenesis of osteoarthritis. The Medical clinics of North America, 93(1): 1-24, xv, 2009.
2. Anderson, D. D.; Chubinskaya, S.; Guilak, F.; Martin, J. A.; Oegema, T. R.; Olson, S. A.; and Buckwalter, J. A.: Post-traumatic osteoarthritis: Improved understanding and opportunities for early intervention. Journal of orthopaedic research: official publication of the Orthopaedic Research Society, 29(6): 802-9, 2011.
3. Lewis, J. S. et al.: Acute joint pathology and synovial inflammation is associated with increased intra-articular fracture severity in the mouse knee. Osteoarthritis and cartilage/OARS, Osteoarthritis Research Society, 2011.
4. Brown, T. D.; Johnston, R. C.; Saltzman, C. L.; Marsh, J. L.; and Buckwalter, J. A.: Posttraumatic osteoarthritis: a first estimate of incidence, prevalence, and burden of disease. J Orthop Trauma, 20(10): 739-44, 2006.
5. AAOS: http://orthoinfo.aaos.org/topic.cfm?topic=a00297. 2009.
6. Bottoni, C.: Anterior Cruciate Ligament Reconstructions in Active-Duty Military Patients. Operative Techniques in Sports Medicine, 13(3): 169-175, 2005.
7. Lohmander, L. S.; Englund, P. M.; Dahl, L. L.; and Roos, E. M.: The long-term consequence of anterior cruciate ligament and meniscus injuries: osteoarthritis. The American journal of sports medicine, 35(10): 1756-69, 2007.
8. Firestein, G. S., and Kelley, W. N.: Kelley's textbook of rheumatology. Edited, Philadelphia, Pa., Saunders/Elsevier, 2009.
9. Nielsen, A. B., and Yde, J.: Epidemiology of acute knee injuries: a prospective hospital investigation. The Journal of trauma, 31(12): 1644-8, 1991.
10. Buckwalter, J. A., and Brown, T. D.: Joint injury, repair, and remodeling: roles in post-traumatic osteoarthritis. Clinical Orthopaedics and Related Research, (423): 7-16, 2004.
11. Roos, H.; Adalberth, T.; Dahlberg, L.; and Lohmander, L. S.: Osteoarthritis of the knee after injury to the anterior cruciate ligament or meniscus: the influence of time and age. Osteoarthritis and cartilage/OARS, Osteoarthritis Research Society, 3(4): 261-7, 1995.
12. Felson, D. T.: Osteoarthritis in 2010: New takes on treatment and prevention. Nature reviews. Rheumatology, 7(2): 75-6, 2011.
13. Lotz, M. K.: New developments in osteoarthritis. Post-traumatic osteoarthritis: pathogenesis and pharmacological treatment options. Arthritis Res Ther, 12(3): 211, 2010.
14. Catterall, J. B.; Stabler, T. V.; Flannery, C. R.; and Kraus, V. B.: Changes in serum and synovial fluid biomarkers after acute injury (NCT00332254). Arthritis Research & Therapy, 12(6): R229, 2010.
15. Hargreaves, D. C.; Horng, T.; and Medzhitov, R.: Control of inducible gene expression by signal-dependent transcriptional elongation. Cell, 138(1): 129-45, 2009.
16. Amir-Zilberstein, L.; Ainbinder, E.; Toube, L.; Yamaguchi, Y.; Handa, H.; and Dikstein, R.: Differential regulation of NF-kappaB by elongation factors is determined by core promoter type. Molecular and cellular biology, 27(14): 5246-59, 2007.
17. Brasier, A. R.: Expanding role of cyclin dependent kinases in cytokine inducible gene expression. Cell cycle, 7(17): 2661-6, 2008.
18. Barboric, M.; Nissen, R. M.; Kanazawa, S.; Jabrane-Ferrat, N.; and Peterlin, B. M.: NF-kappaB binds P-TEFb to stimulate transcriptional elongation by RNA polymerase II. Molecular Cell, 8(2): 327-37, 2001.
19. Malumbres, M.; Pevarello, P.; Barbacid, M.; and Bischoff, J. R.: CDK inhibitors in cancer therapy: what is next? Trends in pharmacological sciences, 29(1): 16-21, 2008.
20. Krystof, V., and Uldrijan, S.: Cyclin-dependent kinase inhibitors as anticancer drugs. Current drug targets, 11(3): 291-302, 2010.
21. Zhou, Q., and Yik, J. H.: The Yin and Yang of P-TEFb regulation: implications for human immunodeficiency virus gene expression and global control of cell growth and differentiation. Microbiology and molecular biology reviews: MMBR, 70(3): 646-59, 2006.
22. Rizzolio, F.; Tuccinardi, T.; Caligiuri, I.; Lucchetti, C.; and Giordano, A.: CDK inhibitors: from the bench to clinical trials. Current drug targets, 11(3): 279-90, 2010.
23. Karaman, M. W. et al.: A quantitative analysis of kinase inhibitor selectivity. Nature biotechnology, 26(1): 127-32, 2008.
24. Phelps, M. A. et al.: Clinical response and pharmacokinetics from a phase 1 study of an active dosing schedule of flavopiridol in relapsed chronic lymphocytic leukemia. Blood, 113(12): 2637-45, 2009.
25. Ni, W. et al.: Flavopiridol pharmacogenetics: clinical and functional evidence for the role of SLCO1B1/OATP1B1 in flavopiridol disposition. PLoS ONE, 5(11): e13792, 2010.
26. Byrd, J. C. et al.: Flavopiridol administered using a pharmacologically derived schedule is associated with marked clinical efficacy in refractory, genetically high-risk chronic lymphocytic leukemia. Blood, 109(2): 399-404, 2007.
27. Sekine, C.; Sugihara, T.; Miyake, S.; Hirai, H.; Yoshida, M.; Miyasaka, N.; and Kohsaka, H.: Successful treatment of animal models of rheumatoid arthritis with small-molecule cyclin-dependent kinase inhibitors. Journal of immunology, 180(3): 1954-61, 2008.
28. Glasson, S. S. et al.: Deletion of active ADAMTS5 prevents cartilage degradation in a murinemodel of osteoarthritis. Nature, 434(7033): 644-8, 2005.
29. Kamekura, S. et al.: Osteoarthritis development in novel experimental mouse models induced byknee joint instability. Osteoarthritis and cartilage/OARS, Osteoarthritis Research Society, 13(7): 632-41, 2005.

30. Glasson, S. S.; Blanchet, T. J.; and Morris, E. A.: The surgical destabilization of the medialmeniscus (DMM) model of osteoarthritis in the 129/SvEv mouse. Osteoarthritis and cartilage/OARS, Osteoarthritis Research Society, 15(9): 1061-9, 2007.
31. Poulet, B.; Hamilton, R. W.; Shefelbine, S.; and Pitsillides, A. A.: Characterizing a novel andadjustable noninvasive murine joint loading model. Arthritis & Rheumatism, 63(1): 137-147, 2011.
32. van Osch, G. J.; van der Kraan, P. M.; Blankevoort, L.; Huiskes, R.; and van den Berg, W. B.: Relation of ligament damage with site specific cartilage loss and osteophyte formation incollagenase induced osteoarthritis in mice. The Journal of rheumatology, 23(7): 1227-32, 1996.
33. Joosten, L. A. et al.: Interleukin-18 promotes joint inflammation and induces interleukin-1-drivencartilage destruction. The American journal of pathology, 165(3): 959-67, 2004.
34. Ameye, L. G., and Young, M. F.: Animal models of osteoarthritis: lessons learned while seeking the"""Holy Grail""". Curr Opin Rheumatol, 18(5): 537-47, 2006.
35. Dahlberg, L.; Roos, H.; Saxne, T.; Heinegard, D.; Lark, M. W.; Hoermer, L. A.; and Lohmander, L. S.: Cartilage metabolism in the injured and uninjured knee of the same patient [see comments]. AnnRheum Dis, 53: 823-7, 1994.
36. Glasson, S. S.; Chambers, M. G.; Van Den Berg, W. B.; and Little, C. B.: The OARSI histopathology initiative—recommendations for histological assessments of osteoarthritis in themouse. Osteoarthritis and cartilage/OARS, Osteoarthritis Research Society, 18 Suppl 3: S17-23, 2010.
37. Aigner, T.; Cook, J. L.; Gerwin, N.; Glasson, S. S.; Laverty, S.; Little, C. B.; McIlwraith, W.; and Kraus, V. B.: Histopathology atlas of animal model systems—overview of guiding principles. Osteoarthritis and cartilage/OARS, Osteoarthritis Research Society, 18 Suppl 3: S2-6, 2010.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for reducing or inhibiting inflammation of tissue in response to an inflammatory stimulus, comprising administering locally or intralesionally to a subject having a traumatic joint injury, a local inflammation, or a surgery an effective amount of a CDK9 inhibitor selected from the group consisting of flavopiridol, 4-(3,5-diamino-1H-pyrazol-4-ylazo)-phenol, and 2-(pyridin-4-yl)-1,5,6,7-tetrahydro-4H-pyrrolo[3,2-c]pyridinone, (PHA-767491), or a salt thereof, wherein the administered CDK9 inhibitor suppresses an inflammatory response at or near the site of the traumatic joint injury, local inflammation, or surgery.

2. The method of claim 1, wherein the CDK9 inhibitor or salt thereof suppresses an inflammatory response in a cell or tissue selected from the group consisting of cartilage, chondrocyte, joint, synovial cell, meniscal cell, ligament, and bone.

3. The method of claim 1, wherein the inflammatory response is an acute inflammatory response.

4. The method of claim 1, wherein the inflammatory response is activation of a catabolic pathway in a cell or tissue selected from the group consisting of cartilage, chondrocyte, joint, synovial cell, meniscal cell, ligament, and bone.

5. The method of claim 1, further comprising reducing or inhibiting transcriptional activation of one or more primary response genes.

6. The method of claim 5, wherein the primary response genes comprise one or more of IL-1β, IL-10, inducible nitric oxide synthase (iNOS), IL-6, TNFα, MMP-1, MMP-3, MMP-9, IL-1a, NFKB1, SOD2, CTSS, MMP-13, ADAMTS4 (aggrecanase), CDKN1A, F3, IL-15, ADM, FAS, CD83, EGFR, CFB, IL1RN, CXCL1, BCL2A1, IL-2, BIRC3, PTGS2, ICAM1, NFKB1A, NR4A2, RELA, CSF1, IL-8, TNFRSF1B, CCL5, RELB, VCAM1, REL, CCL2, CD40, CXCL9, CSF2, CXCL2, CSF3, and CXCL10.

7. The method of claim 1, further comprising reducing or inhibiting IL-1β induced gene expression.

8. The method of claim 1, further comprising reducing or inhibiting pain in the treated subject.

9. The method of claim 1, wherein the CDK9 inhibitor or salt thereof is administered within about 10 days of injury.

10. The method of claim 1, wherein the CDK9 inhibitor or salt thereof is administered within about 4 days of injury.

11. The method of claim 1, wherein the CDK9 inhibitor or salt thereof is administered within about 3 days of injury.

12. The method of claim 1, wherein the CDK9 inhibitor or salt thereof is administered within about 2 days of injury.

13. The method of claim 1, wherein the CDK9 inhibitor or salt thereof is administered within about 1 day of injury.

14. The method of claim 1, wherein the CDK9 inhibitor or salt thereof is administered within about 3 hours of injury.

15. The method of claim 1, wherein the administration of CDK9 inhibitor or salt thereof reduces, delays, or inhibits future onset of osteoarthritis.

16. The method of claim 1, wherein suppressing the inflammatory response comprises protecting tissue from the harmful effects of pro-inflammatory cytokines.

17. The method of claim 1, wherein the CDK9 inhibitor or salt thereof is flavopiridol or a salt thereof.

18. The method of claim 1, further comprising repeated or sustained administration of the CDK9 inhibitor or salt thereof.

19. The method of claim 1, wherein the administration of the CDK9 inhibitor decreases pain, decreases swelling, increases joint mobility, or any combination thereof.

20. A method for inhibiting the expression of a primary response gene in a cell, comprising treating the cell with an effective amount of a CDK9 inhibitor or a salt thereof.

21. The method of claim 20, wherein the primary response gene is one or more of IL-1β, IL-10, inducible nitric oxide synthase (iNOS), IL-6, TNFα, MMP-1, MMP-3, MMP-9, IL-1a, NFKB1, SOD2, CTSS, MMP-13, ADAMTS4 (aggrecanase), CDKN1A, F3, IL-15, ADM, FAS, CD83, EGFR, CFB, IL1RN, CXCL1, BCL2A1, IL-2, BIRC3, PTGS2, ICAM1, NFKB1A, NR4A2, RELA, CSF1, IL-8, TNFRSF1B, CCL5, RELB, VCAM1, REL, CCL2, CD40, CXCL9, CSF2, CXCL2, CSF3, and CXCL10.

22. The method of claim 20, wherein the CDK9 inhibitor is selected from the group consisting of: flavopiridol, 4-(3, 5-diamino-1H-pyrazol-4-ylazo)-phenol, and 2-(pyridin-4-yl)-1,5,6,7-tetrahydro-4H-pyrrolo[3,2-c]pyridinone, kPHA-767491), and salts thereof.

23. The method of claim 22, wherein the CDK9 inhibitor is flavopiridol or a salt thereof.

* * * * *